(12) United States Patent
Nikrad et al.

(10) Patent No.: US 10,359,435 B2
(45) Date of Patent: *Jul. 23, 2019

(54) NONALCOHOLIC FATTY LIVER DISEASE (NAFLD) AND NONALCOHOLIC STEATOHEPATITIS (NASH) BIOMARKERS AND USES THEREOF

(71) Applicant: SOMALOGIC, INC., Boulder, CO (US)

(72) Inventors: Malti Nikrad, Boulder, CO (US); Stuart G. Field, Fort Collins, CO (US); Stephen Alaric Williams, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/910,108

(22) Filed: Mar. 2, 2018

(65) Prior Publication Data

US 2018/0259537 A1 Sep. 13, 2018

Related U.S. Application Data

(62) Division of application No. 15/434,738, filed on Feb. 16, 2017, now Pat. No. 9,945,875, which is a division of application No. 14/202,714, filed on Mar. 10, 2014, now Pat. No. 9,612,248.

(60) Provisional application No. 61/787,967, filed on Mar. 15, 2013.

(51) Int. Cl.
*G01N 31/00* (2006.01)
*G01N 33/53* (2006.01)
*G01N 33/68* (2006.01)

(52) U.S. Cl.
CPC ..... *G01N 33/6893* (2013.01); *G01N 33/5308* (2013.01); *G01N 2333/98* (2013.01); *G01N 2800/085* (2013.01); *G01N 2800/50* (2013.01); *G01N 2800/60* (2013.01)

(58) Field of Classification Search
None
See application file for complete search history.

(56) References Cited

U.S. PATENT DOCUMENTS

| | | |
|---|---|---|
| 5,475,096 A | 12/1995 | Gold et al. |
| 5,580,737 A | 12/1996 | Polisky et al. |
| 5,660,985 A | 8/1997 | Pieken et al. |
| 5,705,337 A | 1/1998 | Gold et al. |
| 5,763,177 A | 6/1998 | Gold et al. |
| 6,001,577 A | 12/1999 | Gold et al. |
| 6,242,246 B1 | 6/2001 | Gold et al. |
| 6,291,184 B1 | 9/2001 | Gold et al. |
| 6,458,539 B1 | 10/2002 | Gold et al. |
| 6,458,543 B1 | 10/2002 | Gold et al. |
| 6,503,715 B1 | 1/2003 | Gold et al. |
| 6,544,776 B1 | 4/2003 | Gold et al. |
| 8,232,065 B2 | 7/2012 | Urdea et al. |
| 8,357,497 B2 | 1/2013 | Urdea et al. |
| 9,103,837 B2 | 8/2015 | Nikrad et al. |
| 9,423,403 B2 | 8/2016 | Nikrad et al. |
| 9,612,248 B2* | 4/2017 | Nikrad ............... G01N 33/6893 |
| 9,945,875 B2* | 4/2018 | Nikrad ............... G01N 33/6893 |
| 2008/0311593 A1 | 12/2008 | Younossi et al. |
| 2009/0004667 A1 | 1/2009 | Zichi et al. |
| 2009/0098549 A1 | 4/2009 | Schneider et al. |
| 2012/0077695 A1 | 3/2012 | Ostroff et al. |
| 2012/0101002 A1 | 4/2012 | Riel-Mehan et al. |

FOREIGN PATENT DOCUMENTS

WO  2010000835 A1  1/2010

OTHER PUBLICATIONS

Pearce et al., Biomarker Research, 2013 1:7, pp. 1-11.*
Bell et al., Hepatology, vol. 51, Issue 1, Jan. 2010, pp. 111-120.*
Brunt et al., "Pathology of fatty liver disease," 2007, Modern Pathol., 20: S40-S48.
Musso et al., "Meta-analysis: Natural history of non-alcoholic fatty liver disease (NAFLD) and diagnostic accuracy of non-invasive tests for liver disease severity," Annals of Medicine 2011;43(8):617-49.
Kraemer et al., "From SOMAmer-Based Biomarker Discovery to Diagnostic and Clinical Applications: A SOMAmer-Based, Streamlined Multiplex Proteomic Assay," PLoS One 6(10): e26332.
Sanyal et al., "Pioglitazone, Vitamin E, or Placebo for Nonalcoholic Steatohepatitis," 2010, NEJM, 362: 1675-1685.
Gold et al., "Aptamer-Based Multiplexed Proteomic Technology for Biomarker Discovery," 2010, PLoS ONE 5(12): e15004.
Bell LN, et al. "Serum proteomics and biomarker discovery across the spectrum of nonalcoholic fatty liver disease," Hepatology. Jan. 2010;51(1):111-20.
Hua X, et al., "Low serum sex hormone-binding globulin is associated with nonalcoholic fatty liver disease in type 2 diabetic patients," Clin Endocrinol (Oxf). Jun. 2014;80(6):877-83. Epub Dec. 5, 2013.
International Search Report and Written Opinion of the International Searching Authority for PCT/US2014/022547 dated Oct. 17, 2014.
Invitation to pay additional fees from the International Searching Authority for international application No. PCT/US2014/022547, dated Jul. 8, 2014.
Kleiner DE, et al., "Design and validation of a histological scoring system for nonalcoholic fatty liver disease," Hepatology. Jun. 2005;41(6):1313-21.
Moylan CA, et al., "Hepatic gene expression profiles differentiate presymptomatic patients with mild versus severe nonalcoholic fatty liver disease," Hepatology. Feb. 2014;59(2):471-82. Epub Dec. 13, 2013.

(Continued)

*Primary Examiner* — Lisa V Cook
(74) *Attorney, Agent, or Firm* — McNeill Baur PLLC

(57) ABSTRACT

Methods, compositions, and kits for determining whether a subject has non-alcoholic fatty liver disease (NAFLD) are provided. Methods, compositions, and kits for determining whether a subject has non-alcoholic steatosis are also provided. Methods, compositions, and kits for determining whether a subject has non-alcoholic steatohepatitis (NASH) are also provided.

16 Claims, 15 Drawing Sheets

(56) References Cited

OTHER PUBLICATIONS

Musso G, et al, "Meta-analysis: natural history of non-alcoholic fatty liver disease (NAFLD) and diagnostic accuracy of non-invasive tests for liver disease severity," Ann Med. Dec. 2011;43(8):617-49. Epub Nov. 2, 2010.

Nikrad MP, et al., "Novel serum protein signature associated with non-alcoholic fatty liver disease," 2013.

Polyzos SA, et al. "Sex steroids and sex hormone-binding globulin in postmenopausal women with nonalcoholic fatty liver disease," Hormones (Athens). Jul.-Sep. 2013;12(3):405-16.

Selman L, Hansen S. "Structure and function of collectin liver 1 (CL-L1) and collectin 11 (CL-11, Cl-K1)," Immunobiology. Sep. 2012;217(9):851-63. Epub Feb. 4, 2012.

Shin JY, et al., "Serum sex hormone-binding globulin levels are independently associated with nonalcoholic fatty liver disease in people with type 2 diabetes," Diabetes Res Clin Pract. Oct. 2011;94(1):156-62. Epub Sep. 8, 2011.

Tian GX, et al., "Oestradiol is a protective factor for non-alcoholic fatty liver disease in healthy men," Obes Rev. Apr. 2012;13(4):381-7. Epub Jan. 12, 2012.

Y. Yilmaz, "Review Article: is Non-alcoholic Fatty Liver Disease a Spectrum, or are Steatosis and Non-alcoholic Steatohepatitis Distinct Conditions?" Alimentary Pharmacol. Ther., 2012; 36(9):815-823.

Steven G. Pearce et al., "Noninvasive biomarkers for the diagnosis of steatohepatitis and advanced fibrosis in NAFLD," Biomarker Research 2013, 1:7, pp. 1-11.

Lauren N. Bell et al., "Serum proteomics and biomarker discovery across the sprectrum of nonalcoholic fatty liver disease," Hepatology, 51(1):111-120, Jan. 2010.

Stefania Varchetta et al., "Lack of Siglec-7 expression identifies a dysfunctional natural killer cell subset associated with liver inflammation and fibrosis in chronic HCV infection," Gut, Dec. 16, 2015, Abstract only.

M. Tascilar et al., "Role of tumor markers and mutations in cells and pancreatic juice in the diagnosis of pancreatic cancer," Annals of Oncology, 10 Suppl. 4:S107-S110, 1999.

Melvyn S. Tockman, "Considerations in Bringing a Cancer Biomarker to Clinical Application," Cancer Research (Suppl.), 52:2711s-2718s, 1992.

* cited by examiner

NONALCOHOLIC FATTY LIVER DISEASE (NAFLD) AND NONALCOHOLIC STEATOHEPATITIS (NASH) BIOMARKERS AND USES THEREOF

This application is a divisional of U.S. application Ser. No. 15/434,738, filed Feb. 16, 2017, now U.S. Pat. No. 9,945,875, issued Apr. 17, 2018, which is a division of U.S. application Ser. No. 14/202,714, filed Mar. 10 2014, now U.S. Pat No. 9,612,248, issued Apr. 4, 2017, which claims the benefit of U.S. Provisional Application No. 61/787,967, filed Mar. 15, 2013, each of which is incorporated by reference herein in its entirety for any purpose.

FIELD OF THE INVENTION

The present application relates generally to the detection of biomarkers and the characterization of nonalcoholic fatty liver disease (NAFLD), for example, to identify subjects with steatosis and nonalcoholic steatohepatitis (NASH). In various embodiments, the invention relates to one or more biomarkers, methods, devices, reagents, systems, and kits for characterizing NAFLD and NASH in an individual.

BACKGROUND

The following description provides a summary of information and is not an admission that any of the information provided or publications referenced herein is prior art to the present application.

Nonalcoholic fatty liver disease (NAFLD) is defined as the presence of hepatic steatosis, with or without inflammation and fibrosis, in the absence of alcohol history. NAFLD is subdivided into nonalcoholic fatty liver (NAFL) and nonalcoholic steatohepatitis (NASH). In NAFL, hepatic steatosis is present without evidence of significant inflammation, whereas in NASH, hepatic steatosis is associated with hepatic inflammation that may be histologically indistinguishable from alcoholic steatohepatitis.

NAFLD has become an epidemic worldwide and is the leading cause of liver disease in North America, as a result of the rapidly increasing prevalence of obesity. However, accurate population-based data on the incidence of NAFL and NASH are sparse, in part because the diagnosis requires histopathologic documentation. Major risk factors for NAFLD are central obesity, type 2 diabetes mellitus, high levels of triglyceride (fat) in the blood, and high blood pressure. In the U.S., NAFLD is present in 20-40% of the population and NASH is present in about 25% of the obese population. Ten to twenty-nine percent of the NASH patients develop cirrhosis and 4-27% of those develop hepatic cancer.

Most people with NASH have no symptoms. Some may have right upper quadrant pain, hepatomegaly, or nonspecific symptoms such as abdominal discomfort, weakness, fatigue or malaise. A doctor or nurse may suspect the presence of NASH from the results of routine blood tests. In NAFLD, liver enzymes aspartate aminotransferase (AST) and alanine aminotransferase (ALT) are often high.

The current gold standard to confirm NASH is a histological evaluation of liver biopsy, which is expensive, invasive, and can cause pain, hemorrhage, or even death.

A simple blood test that would identify and distinguish the various stages of both NAFLD and NASH (and thereby reduce the need for liver biopsy) would be highly desirable.

SUMMARY

In some embodiments, methods of determining whether a subject has nonalcoholic fatty liver disease (NAFLD) are provided. In some embodiments, methods of identifying subjects with steatosis are provided. In some embodiments, methods of determining the severity of steatosis are provided.

In some embodiments, methods of determining whether a subject has nonalcoholic steatohepatitis (NASH) are provided. In some embodiments, methods of identifying subjects with NASH are provided. In some embodiments, methods of distinguishing subjects with NASH from subjects with steatosis are provided. In some embodiments, methods of determining the severity of NASH are provided.

In some embodiments, methods of determining whether a subject has non-alcoholic fatty liver disease (NAFLD) are provided. In some embodiments, a method comprises detecting the level of at least one, at least two, at least three, at least four, at least five, at least six, at least seven, at least eight, at least nine, at least ten, or eleven biomarkers selected from ACY, SHBG, CTSZ, MET, GSN, LGALS3BP, PLAT, CHL1, SERPINC1, SIGLEC7, and SIGLEC14, in a sample from the subject. In some embodiments, a level of at least one biomarker selected from ACY, CTSZ, LGALS3BP, SIGLEC7, SIGLEC14, and PLAT that is higher than a control level of the respective biomarker indicates that the subject has NAFLD. In some embodiments, a level of at least one biomarker selected from SHBG, MET, GSN, CHL1, and SERPINC1 that is lower than a control level of the respective biomarker indicates that the subject has NAFLD. In some embodiments, the method comprises determining whether a subject has steatosis. In some embodiments, the steatosis is mild, moderate, or severe steatosis. In some embodiments, the method comprises detecting at least one, at least two, or three biomarkers selected from ACY, SHBG, and SIGLEC14. In some embodiments, the method comprises determining whether a subject has non-alcoholic steatohepatitis (NASH). In some embodiments, the NASH is stage 1, 2, 3, or 4 NASH. In some embodiments, the method comprises detecting at least one, at least two, at least three, at least four, at least five, at least six, or seven biomarkers selected from ACY, SHBG, CTSZ, MET, GSN, LGALS3BP, and SIGLEC7. In some embodiments, the method comprises detecting of at least one, at least two, at least three, at least four, at least five, at least six, at least seven, at least eight, or nine biomarkers selected from ACY, SHBG, CTSZ, MET, GSN, LGALS3BP, PLAT, CHL1, and SERPINC1.

In some embodiments, methods of determining whether a subject with non-alcoholic steatosis has non-alcoholic steatohepatitis (NASH) are provided. In some embodiments, a method comprises detecting the level of at least one, at least two, at least three, at least four, at least five, at least six, at least seven, at least eight, or nine biomarker selected from C7, PPID, IGFBP3, SIGLEC14, AIMP1, TOP1, COLEC11, CA6, and STX1A in a sample from the subject. In some embodiments, a level of at least one biomarker selected from C7, COLEC11, PPID, and SIGLEC14 that is higher than a control level of the respective biomarker indicates that the subject has NASH. In some embodiments, a level of at least one biomarker selected from IGFBP3, AIMP1, TOP1, CA6, and STX1A that is lower than a control level of the respective biomarker, indicates that the subject has NASH. In some embodiments, the subject has mild, moderate, or severe steatosis. In some embodiments, the NASH is stage 1, 2, 3, or 4 NASH. In some embodiments, the NASH is stage 2, 3, or 4 NASH. In some embodiments, the method comprises detecting the levels of at least one, at least two, at least three, or four biomarkers selected from C7, COLEC11, PPID, and IGFBP3. In some embodiments, the method comprises detecting the levels of at least one, at least two, at least three, at least four, at least five, or six biomarkers selected from SIGLEC14, AIMP1, TOP1, COLEC11, CA6, and STX1A.

In some embodiments, methods of monitoring a subject with non-alcoholic steatosis for development of NASH are provided. In some embodiments, a method comprises detecting the level of at least one, at least two, at least three, at least four, at least five, at least six, at least seven, at least eight, or nine biomarkers selected from C7, PPID, IGFBP3, SIGLEC14, AIMP1, TOP1, COLEC11, CA6, and STX1A in a sample from the subject. In some embodiments, a level of at least one biomarker selected from C7, COLEC11, PPID, and SIGLEC14 that is higher than a control level of the respective biomarker indicates that the subject has NASH. In some embodiments, a level of at least one biomarker selected from IGFBP3, AIMP1, TOP1, CA6, and STX1A that is lower than a control level of the respective biomarker, indicates that the subject has NASH. In some embodiments, the subject has mild, moderate, or severe steatosis. In some embodiments, the NASH is stage 1, 2, 3, or 4 NASH. In some embodiments, the NASH is stage 2, 3, or 4 NASH. In some embodiments, the method comprises detecting the levels of at least one, at least two, at least three, or four biomarkers selected from C7, COLEC11, PPID, and IGFBP3. In some embodiments, the method comprises detecting the levels of at least one, at least two, at least three, at least four, at least five, or six biomarkers selected from SIGLEC14, AIMP1, TOP1, COLEC11, CA6, and STX1A.

In some embodiments, methods of determining whether a subject has NAFLD are provided, wherein the method comprises detecting the level of at least one, at least two, at least three, at least four, at least five, at least six, at least seven, at least eight, at least nine, or at least ten biomarkers selected from the biomarkers in Table 7. In some embodiments, a level of a biomarker in Table 7 other than SHBG and GSN that is higher than a control level of the respective biomarker indicates that the subject has NAFLD. In some embodiments, a level of at least one biomarker selected from SHBG and GSN that is lower than a control level of the respective biomarker, indicates that the subject has NAFLD. In some embodiments, the method comprises determining whether a subject has NASH.

In any of the embodiments described herein, the subject may be at risk of developing NAFLD. In any of the embodiments described herein, the subject may be at risk of developing steatosis. In any of the embodiments described herein, the subject may be at risk of developing NASH. In any of the embodiments described herein, the subject may have an NAFLD comorbidity selected from obesity, abdominal obesity, metabolic syndrome, cardiovascular disease, and diabetes. In any of the embodiments described herein, the subject may be obese.

In any of the embodiments described herein, at least one biomarker may be a protein biomarker. In any of the embodiments described herein, each biomarker may be a protein biomarker. In some embodiments, a method comprises contacting biomarkers of the sample from the subject with a set of biomarker capture reagents, wherein each biomarker capture reagent of the set of biomarker capture reagents specifically binds to a different biomarker being detected. In some embodiments, each biomarker capture reagent is an antibody or an aptamer. In some embodiments, each biomarker capture reagent is an aptamer. In some embodiments, at least one aptamer is a slow off-rate aptamer. In some embodiments, at least one slow off-rate aptamer comprises at least one, at least two, at least three, at least four, at least five, at least six, at least seven, at least eight, at least nine, or at least 10 nucleotides with modifications. In some embodiments, each slow off-rate aptamer binds to its target protein with an off rate (t½) of ≥30 minutes, ≥60 minutes, ≥90 minutes, ≥120 minutes, ≥150 minutes, ≥180 minutes, ≥210 minutes, or ≥240 minutes.

In any of the embodiments described herein, the sample may be a blood sample. In any of the embodiments described herein, the sample may be selected from a serum sample and a plasma sample.

In any of the embodiments described herein, if the subject has NAFLD or NASH, the subject may be recommended a regimen selected from weight loss, blood sugar control, and alcohol avoidance. In any of the embodiments described herein, if the subject has NAFLD or NASH, the subject may be recommended for gastric bypass surgery. In any of the embodiments described herein, if the subject has NAFLD or NASH, the subject may be prescribed at least one therapeutic agent selected from pioglitazone, vitamin E, and metformin.

In some embodiments, a method described herein is for the purpose of determining a medical insurance premium or life insurance premium. In some embodiments, a method further comprises determining a medical insurance premium or life insurance premium. In some embodiments, a method described herein further comprises using information resulting from the method to predict and/or manage the utilization of medical resources.

In some embodiments, kits are provided. In some embodiments, a kit comprises at least one, at least two, at least three, at least four, at least five, at least six, at least seven, at least eight, at least nine, at least ten, or eleven aptamers that specifically bind to a target protein selected from ACY, SHBG, CTSZ, MET, GSN, LGALS3BP, PLAT, CHL1, SERPINC1, SIGLEC7, and SIGLEC14. In some embodiments, a kit comprises at least one, at least two, at least three, at least four, at least five, at least six, at least seven, at least eight, at least nine, or at least ten aptamers that specifically bind to a target protein selected from the proteins in Table 7. In some embodiments, each aptamer specifically binds to a different target protein.

In some embodiments, a kit comprises at least one, at least two, or three aptamers that specifically bind to a target protein selected from ACY, SHBG, and SIGLEC14. In some embodiments, a kit comprises at least one, at least two, at least three, at least four, at least five, at least six, or seven aptamers that specifically bind to a target protein selected from ACY, SHBG, CTSZ, MET, GSN, LGALS3BP, and SIGLEC7. In some embodiments, a kit comprises at least one, at least two, at least three, at least four, at least five, at least six, at least seven, at least eight, or nine aptamers that specifically bind to a target protein selected from ACY, SHBG, CTSZ, MET, GSN, LGALS3BP, PLAT, CHL1, and SERPINC1.

In some embodiments, a kit is provided, wherein the kit comprises at least one, at least two, at least three, at least four, at least five, at least six, at least seven, at least eight, or nine aptamers that specifically bind to a target protein selected from C7, PPID, IGFBP3, SIGLEC14, AIMP1, TOP1, COLEC11, CA6, and STX1A. In some embodiments, each aptamer binds to a different target protein.

In some embodiments, a kit comprises at least one, at least two, at least three, or four aptamers that specifically bind to a target protein selected from C7, COLEC11, PPID, and IGFBP3. In some embodiments, a kit comprises at least one, at least two, at least three, at least four, at least five, or six aptamers that specifically bind to a target protein selected from SIGLEC14, AIMP1, TOP1, COLEC11, CA6, and STX1A.

In any of the embodiments described herein, at least one aptamer may be a slow off-rate aptamer. In any of the embodiments described herein, each aptamer may be a slow off-rate aptamer. In some embodiments, at least one slow off-rate aptamer comprises at least one, at least two, at least three, at least four, at least five, at least six, at least seven, at least eight, at least nine, or at least 10 nucleotides with hydrophobic modifications. In some embodiments, each slow off-rate aptamer binds to its target protein with an off rate (t½) of ≥30 minutes, ≥60 minutes, ≥90 minutes, ≥120 minutes, ≥150 minutes, ≥180 minutes, ≥210 minutes, or ≥240 minutes.

In some embodiments, compositions are provided. In some such embodiments, a composition comprises proteins of a sample from a subject and at least one, at least two, at least three, at least four, at least five, at least six, at least seven, at least eight, at least nine, at least ten, or eleven aptamers that specifically bind to a target protein selected from ACY, SHBG, CTSZ, MET, GSN, LGALS3BP, PLAT, CHL1, SERPINC1, SIGLEC7, and SIGLEC14. In some embodiments, a composition comprises proteins of a sample and at least one, at least two, at least three, at least four, at least five, at least six, at least seven, at least eight, at least nine, or at least ten aptamers that specifically bind to a target protein selected from the proteins in Table 7. In some embodiments, each aptamer specifically binds to a different target protein.

In some embodiments, a composition comprises at least one, at least two, or three aptamers that specifically bind to a target protein selected from ACY, SHBG, and SIGLEC14. In some embodiments, a composition comprises at least one, at least two, at least three, at least four, at least five, at least six, or seven aptamers that specifically bind to a target protein selected from ACY, SHBG, CTSZ, MET, GSN, LGALS3BP, and SIGLEC7. In some embodiments, a composition comprises at least one, at least two, at least three, at least four, at least five, at least six, at least seven, at least eight, or nine aptamers that specifically bind to a target protein selected from ACY, SHBG, CTSZ, MET, GSN, LGALS3BP, PLAT, CHL1, and SERPINC1.

In some embodiments, a composition is provided that comprises proteins of a sample from a subject and at least one, at least two, at least three, at least four, at least five, at least six, at least seven, at least eight, or nine aptamers that specifically bind to a target protein selected from C7, PPID, IGFBP3, SIGLEC14, AIMP1, TOP1, COLEC11, CA6, and STX1A. In some embodiments, each aptamer binds to a different target protein.

In some embodiments, a composition comprises at least one, at least two, at least three, or four aptamers that specifically bind to a target protein selected from C7, COLEC11, PPID, and IGFBP3. In some embodiments, a composition comprises at least one, at least two, at least three, at least four, at least five, or six aptamers that specifically bind to a target protein selected from SIGLEC14, AIMP1, TOP1, COLEC11, CA6, and STX1A.

In any of the embodiments described herein, the sample may be a blood sample. In any of the embodiments described herein, the sample may be selected from a serum sample and a plasma sample.

In any of the embodiments described herein, at least one aptamer may be a slow off-rate aptamer. In any of the embodiments described herein, each aptamer may be a slow off-rate aptamer. In some embodiments, at least one slow off-rate aptamer comprises at least one, at least two, at least three, at least four, at least five, at least six, at least seven, at least eight, at least nine, or at least 10 nucleotides with hydrophobic modifications. In some embodiments, each slow off-rate aptamer binds to its target protein with an off rate (t½) of ≥30 minutes, ≥60 minutes, ≥90 minutes, ≥120 minutes, ≥150 minutes, ≥180 minutes, ≥210 minutes, or ≥240 minutes.

In any of the embodiments described herein, each biomarker may be a protein biomarker. In any of the embodiments described herein, the method may comprise contacting biomarkers of the sample from the subject with a set of biomarker capture reagents, wherein each biomarker capture reagent of the set of biomarker capture reagents specifically binds to a biomarker being detected. In some embodiments, each biomarker capture reagent of the set of biomarker capture reagents specifically binds to a different biomarker being detected. In any of the embodiments described herein, each biomarker capture reagent may be an antibody or an aptamer. In any of the embodiments described herein, each biomarker capture reagent may be an aptamer. In any of the embodiments described herein, at least one aptamer may be a slow off-rate aptamer. In any of the embodiments described herein, at least one slow off-rate aptamer may comprise at least one, at least two, at least three, at least four, at least five, at least six, at least seven, at least eight, at least nine, or at least 10 nucleotides with modifications. In some embodiments, the modifications are hydrophobic modifications. In some embodiments, the modifications are hydrophobic base modifications. In some embodiments, one or more of the modifications may be selected from the modifications shown in FIG. 11. In some embodiments, each slow off-rate aptamer binds to its target protein with an off rate (t½) of ≥30 minutes, ≥60 minutes, ≥90 minutes, ≥120 minutes, ≥150 minutes, ≥180 minutes, ≥210 minutes, or ≥240 minutes.

In any of the embodiments described herein, the sample may be a blood sample. In some embodiments, the blood sample is selected from a serum sample and a plasma sample.

In any of the embodiments, described herein, the sample in a composition may be a blood sample. In some embodiments, the blood sample is selected from a serum sample and a plasma sample.

In any of the embodiments described herein, a kit or composition may comprise at least one aptamer that is a slow off-rate aptamer. In any of the embodiments described herein, each aptamer of a kit or composition may be a slow off-rate aptamer. In some embodiments, at least one slow off-rate aptamer comprises at least one, at least two, at least three, at least four, at least five, at least six, at least seven, at least eight, at least nine, or at least 10 nucleotides with modifications. In some embodiments, at least one nucleotide with a modification is a nucleotide with a hydrophobic base modification. In some embodiments, each nucleotide with a modification is a nucleotide with a hydrophobic base modification. In some embodiments, each hydrophobic base modification is independently selected from the modification in FIG. 11. In some embodiments, each slow off-rate aptamer in a kit binds to its target protein with an off rate (t½) of ≥30 minutes, ≥60 minutes, ≥90 minutes, ≥120 minutes, ≥150 minutes, ≥180 minutes, ≥210 minutes, or ≥240 minutes.

DETAILED DESCRIPTION

Figure 1:
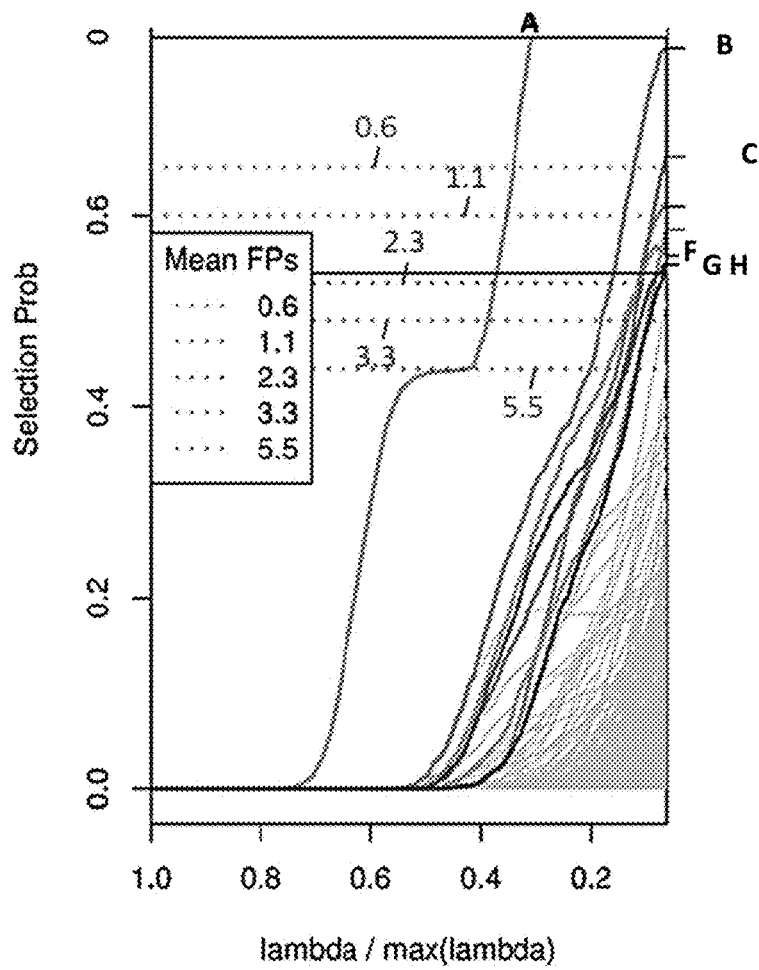
FIG. 1 shows stability selection paths of the steatosis classifier, as described in Example 2.

While the invention will be described in conjunction with certain representative embodiments, it will be understood that the invention is defined by the claims, and is not limited to those embodiments.

One skilled in the art will recognize many methods and materials similar or equivalent to those described herein may be used in the practice of the present invention. The present invention is in no way limited to the methods and materials described.

Unless defined otherwise, technical and scientific terms used herein have the meaning commonly understood by one of ordinary skill in the art to which this invention belongs. Although any methods, devices, and materials similar or equivalent to those described herein can be used in the practice of the invention, certain methods, devices, and materials are described herein.

All publications, published patent documents, and patent applications cited herein are hereby incorporated by reference to the same extent as though each individual publication, published patent document, or patent application was specifically and individually indicated as being incorporated by reference.

As used in this application, including the appended claims, the singular forms "a," "an," and "the" include the plural, unless the context clearly dictates otherwise, and may be used interchangeably with "at least one" and "one or more." Thus, reference to "an aptamer" includes mixtures of aptamers, reference to "a probe" includes mixtures of probes, and the like.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements may include other elements not expressly listed.

The present application includes biomarkers, methods, devices, reagents, systems, and kits for determining whether a subject has NAFLD. The present application also includes biomarkers, methods, devices, reagents, systems, and kits for determining whether a subject has NASH. In some embodiments, biomarkers, methods, devices, reagents, systems, and kits are provided for determining whether a subject with NAFLD has NASH.

In some embodiments, one or more biomarkers are provided for use either alone or in various combinations to determine whether a subject has NAFLD. As described in detail below, exemplary embodiments include the biomarkers provided in Tables 3, 4, 6, and 7, which were identified using a multiplex aptamer-based assay. Table 3 lists nine biomarkers that are useful for distinguishing samples obtained from normal obese individuals from samples from individuals with NAFLD. Table 4 lists four biomarkers that are useful for distinguishing samples obtained from individuals with steatosis from samples from individuals with NASH stages 2, 3, and 4. Tables 6 and 7 list additional biomarkers that may be used in any combination with one another and/or with the biomarkers from Tables 3 and 4. In some embodiments, a subset of biomarkers from Tables 3, 4, 6, and 7 are combined into a panel shown in Table 5.

In some embodiments, one or more biomarkers are provided for use either alone or in various combinations to determine whether a subject has steatosis. In some embodiments, the subject is obese. As described in detail below, exemplary embodiments include the biomarkers provided in Table 3, which were identified using a multiplex aptamer-based assay. Table 3 lists four biomarkers that are useful for distinguishing samples obtained from obese individuals from samples from individuals with steatosis. In addition, one or more of the biomarkers in Table 3 may be used in combination with one or more biomarkers from Table 4 and/or Table 6 and/or Table 7, with or without one or more biomarkers not listed in any of Tables 3, 4, 6, or 7 in a method described herein.

In some embodiments, one or more biomarkers are provided for use either alone or in various combinations to determine whether a subject has NASH of any stage. In some embodiments, one or more biomarkers are provided for use either alone or in various combinations to determine whether a subject has stage 2, 3, or 4 NASH. In some embodiments, the subject is already known to have steatosis. As described in detail below, exemplary embodiments include the biomarkers provided in Table 4, which were identified using a multiplex aptamer-based assay. Table 4 lists four biomarkers that are useful for distinguishing samples obtained from individuals with steatosis from samples from individuals with NASH. In addition, one or more of the biomarkers in Table 4 may be used in combination with one or more biomarkers from Table 3 and/or Table 6 and/or Table 7, with or without one or more biomarkers not listed in any of Tables 3, 4, 6, or 7 in a method described herein.

In some embodiments, the number and identity of biomarkers in a panel are selected based on the sensitivity and specificity for the particular combination of biomarker values. The terms "sensitivity" and "specificity" are used herein with respect to the ability to correctly classify an individual, based on one or more biomarker levels detected in a biological sample, as having the disease or not having the disease. In some embodiments, the terms "sensitivity" and "specificity" may be used herein with respect to the ability to correctly classify an individual, based on one or more biomarker levels detected in a biological sample, as having steatosis or not having steatosis. In such embodiments, "sensitivity" indicates the performance of the biomarker(s) with respect to correctly classifying individuals with steatosis. "Specificity" indicates the performance of the biomarker(s) with respect to correctly classifying individuals who do not have steatosis. For example, 85% specificity and 90% sensitivity for a panel of biomarkers used to test a set of control samples (such as samples from healthy individuals or subjects known not to have steatosis) and test samples (such as samples from individuals with steatosis) indicates that 85% of the control samples were correctly classified as control samples by the panel, and 90% of the test samples were correctly classified as test samples by the panel.

In some embodiments, the terms "sensitivity" and "specificity" may be used herein with respect to the ability to correctly classify an individual, based on one or more biomarker levels detected in a biological sample, as having NASH (or stage 2, 3, or 4 NASH) or having steatosis. "Sensitivity" indicates the performance of the biomarker(s) with respect to correctly classifying individuals with NASH (or stage 2, 3, or 4 NASH). "Specificity" indicates the performance of the biomarker(s) with respect to correctly classifying individuals who do not have NASH (or do not have stage 2, 3, or 4 NASH). For example, 85% specificity and 90% sensitivity for a panel of biomarkers used to test a set of control samples (such as samples from individuals with steatosis) and test samples (such as samples from individuals with NASH, or stage 2, 3, or 4 NASH) indicates that 85% of the control samples were correctly classified as control samples by the panel, and 90% of the test samples were correctly classified as test samples by the panel.

In some embodiments, overall performance of a panel of one or more biomarkers is represented by the area-under-the-curve (AUC) value. The AUC value is derived from receiver operating characteristic (ROC) curve, which are exemplified herein. The ROC curve is the plot of the true positive rate (sensitivity) of a test against the false positive rate (1-specificity) of the test. The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., normal individuals and individuals with NAFLD, or individuals with steatosis and individuals with NASH). ROC curves are useful for plotting the performance of a particular feature (e.g., any of the biomarkers described herein and/or any item of additional biomedical information) in distinguishing between two populations. Typically, the feature data across the entire population are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve.

In some embodiments, a method comprises detecting the level of at least one biomarker listed in Table 3, 4, 6, or 7 in a sample from a subject for determining whether a subject has NAFLD. In some such embodiments, the method comprises contacting the sample or a portion of the sample from the subject with at least one capture reagent, wherein each capture reagent specifically binds a biomarker whose levels are being detected. In some embodiments, the method comprises contacting the sample, or proteins from the sample, with at least one aptamer, wherein each aptamer specifically binds a biomarker whose levels are being detected.

In some embodiments, a method comprises detecting the level of at least one, at least two, at least three, at least four, at least five, at least six, at least seven, at least eight, at least nine, at least ten, or eleven biomarkers selected from ACY, SHBG, CTSZ, MET, GSN, LGALS3BP, PLAT, CHL1, SERPINC1, SIGLEC7, and SIGLEC14 in a sample from a subject, wherein a level of at least one biomarker selected from ACY, CTSZ, LGALS3BP, SIGLEC7, SIGLEC14, and PLAT that is higher than a control level of the respective biomarker, and/or a level of at least one biomarker selected from SHBG, MET, GSN, CHL1, and SERPINC1 that is lower than a control level of the respective biomarker, indicates that the subject has NAFLD. In some embodiments, the subject is an obese subject. In some embodiments, the method comprises determining whether the subject has steatosis, and/or determining whether the steatosis is mild, moderate or severe. In some such embodiments, the method comprises detecting the level of at least one, at least two, or three biomarkers selected from ACY, SHBG, and SIGLEC14. In some embodiments, the method comprises determining whether the subject has NASH, such as stage 1, 2, 3, or 4 NASH. In some such embodiments, the method comprises detecting the level of at least one, at least two, at least three, at least four, at least five, at least six, or seven biomarkers selected from ACY, SHBG, CTSZ, MET, GSN, LGALS3BP, and SIGLEC7. In some embodiments, a method comprises determining whether a subject has NAFLD, which may be either steatosis or NASH. In some such embodiments, the method comprises detecting the levels of at least one, at least two, at least three, at least four, at least five, at least six, at least seven, at least eight, or nine biomarkers selected from ACY, SHBG, CTSZ, MET, GSN, LGALS3BP, PLAT, CHL1, and SERPINC1.

In some embodiments, a method comprises detecting the level of at least one, at least two, at least three, at least four, at least five, at least six, at least seven, at least eight, at least nine, or at least ten biomarkers selected from the biomarkers in Table 7. In some embodiments, a level of a biomarker in Table 7 other than SHBG and GSN that is higher than a control level of the respective biomarker, and/or a level of at least one biomarker selected from SHBG and GSN that is lower than a control level of the respective biomarker, indicates that the subject has NAFLD.

The biomarkers identified herein provide a number of choices for subsets or panels of biomarkers that can be used to effectively identify NAFLD. Selection of the appropriate number of such biomarkers may depend on the specific combination of biomarkers chosen. In addition, in any of the methods described herein, except where explicitly indicated, a panel of biomarkers may comprise additional biomarkers not shown in Table 3, 4, 6, or 7.

In some embodiments, a method comprises detecting the level of at least one, at least two, at least three, at least four, at least five, at least six, at least seven, at least eight, or nine biomarkers selected from C7, PPID, IGFBP3, SIGLEC14, AIMP1, TOP1, COLEC11, CA6, and STX1A in a sample from a subject, wherein a level of at least one biomarker selected from C7, COLEC11, PPID, and SIGLEC14 that is higher than a control level of the respective biomarker, and/or a level of at least one biomarker selected from IGFBP3, AIMP1, TOP1, CA6, and STX1A that is lower than a control level of the respective biomarker, indicates that the subject has NASH. In some embodiments, the subject is obese. In some embodiments, the subject has already been determined to have steatosis, which may be mild, moderate, or severe steatosis. In some embodiments, the NASH is stage 1, 2, 3, or 4 NASH. In some embodiments, the NASH is stage 2, 3, or 4 NASH. In some such embodiments, the method comprises detecting the levels of at least one, at least two, at least three, or four biomarkers selected from C7, COLEC11, PPID, and IGFBP3.

In some embodiments, a method comprises detecting the level of at least one biomarker listed in Table 3, 4, 6, or 7 in a sample from a subject for determining whether a subject has NASH, or stage 2, 3, or 4 NASH. In some such embodiments, the method comprises contacting the sample or a portion of the sample from the subject with at least one capture reagent, wherein each capture reagent specifically binds a biomarker whose levels are being detected. In some embodiments, the method comprises contacting the sample, or proteins from the sample, with at least one aptamer, wherein each aptamer specifically binds a biomarker whose levels are being detected.

The biomarkers identified herein provide a number of choices for subsets or panels of biomarkers that can be used to effectively identify NASH, or stage 2, 3, or 4 NASH. Selection of the appropriate number of such biomarkers may depend on the specific combination of biomarkers chosen. In addition, in any of the methods described herein, except where explicitly indicated, a panel of biomarkers may comprise additional biomarkers not shown in Table 3, 4, 6, or 7.

As used herein, "nonalcoholic fatty liver disease" or "NAFLD" refers to a condition in which fat is deposited in the liver (hepatic steatosis), with or without inflammation and fibrosis, in the absence of excessive alcohol use.

As used herein, "steatosis" and "non-alcoholic steatosis" are used interchangeably, and include mild, moderate, and severe steatosis, without inflammation or fibrosis, in the absence of excessive alcohol use. Table 1 shows exemplary classification of mild, moderate, and severe steatosis.

As used herein, "nonalcoholic steatohepatitis" or "NASH" refers to NAFLD in which there is inflammation and/or fibrosis in the liver. NASH may be divided into four stages. Exemplary methods of determining the stage of NASH are described, for example, in Kleiner et al., 2005, *Hepatology*, 41(6):1313-1321, and Brunt et al., 2007, *Modern Pathol.*, 20: S40-S48. Table 1 shows exemplary classification of stage 1, 2, 3, and 4 NASH.

As used herein, "obese" with reference to a subject refers to a subject with a BMI of 30 or greater.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, urine, saliva, peritoneal washings, ascites, cystic fluid, glandular fluid, lymph fluid, bronchial aspirate, synovial fluid, joint aspirate, organ secretions, cells, a cellular extract, and cerebrospinal fluid. This also includes experimentally separated fractions of all of the preceding. For example, a blood sample can be fractionated into serum, plasma, or into fractions containing particular types of blood cells, such as red blood cells or white blood cells (leukocytes). In some embodiments, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Exemplary tissues susceptible to fine needle aspiration include lymph node, lung, thyroid, breast, pancreas, and liver. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual.

Further, in some embodiments, a biological sample may be derived by taking biological samples from a number of individuals and pooling them, or pooling an aliquot of each individual's biological sample. The pooled sample may be treated as described herein for a sample from a single individual, and, for example, if a poor prognosis is established in the pooled sample, then each individual biological sample can be re-tested to determine which individual(s) have steatosis and/or NASH.

"Target", "target molecule", and "analyte" are used interchangeably herein to refer to any molecule of interest that may be present in a biological sample. A "molecule of interest" includes any minor variation of a particular molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule", "target", or "analyte" refers to a set of copies of one type or species of molecule or multi-molecular structure. "Target molecules", "targets", and "analytes" refer to more than one type or species of molecule or multi-molecular structure. Exemplary target molecules include proteins, polypeptides, nucleic acids, carbohydrates, lipids, polysaccharides, glycoproteins, hormones, receptors, antigens, antibodies, affybodies, antibody mimics, viruses, pathogens, toxic substances, substrates, metabolites, transition state analogs, cofactors, inhibitors, drugs, dyes, nutrients, growth factors, cells, tissues, and any fragment or portion of any of the foregoing. In some embodiments, a target molecule is a protein, in which case the target molecule may be referred to as a "target protein."

As used herein, a "capture agent" or "capture reagent" refers to a molecule that is capable of binding specifically to a biomarker. A "target protein capture reagent" refers to a molecule that is capable of binding specifically to a target protein. Nonlimiting exemplary capture reagents include aptamers, antibodies, adnectins, ankyrins, other antibody mimetics and other protein scaffolds, autoantibodies, chimeras, small molecules, nucleic acids, lectins, ligand-binding receptors, imprinted polymers, avimers, peptidomimetics, hormone receptors, cytokine receptors, synthetic receptors, and modifications and fragments of any of the aforementioned capture reagents. In some embodiments, a capture reagent is selected from an aptamer and an antibody.

The term "antibody" refers to full-length antibodies of any species and fragments and derivatives of such antibodies, including Fab fragments, F(ab')2 fragments, single chain antibodies, Fv fragments, and single chain Fv fragments. The term "antibody" also refers to synthetically-derived antibodies, such as phage display-derived antibodies and fragments, affybodies, nanobodies, etc.

As used herein, "marker" and "biomarker" are used interchangeably to refer to a target molecule that indicates or is a sign of a normal or abnormal process in an individual or of a disease or other condition in an individual. More specifically, a "marker" or "biomarker" is an anatomic, physiologic, biochemical, or molecular parameter associated with the presence of a specific physiological state or process, whether normal or abnormal, and, if abnormal, whether chronic or acute. Biomarkers are detectable and measurable by a variety of methods including laboratory assays and medical imaging. In some embodiments, a biomarker is a target protein.

As used herein, "biomarker level" and "level" refer to a measurement that is made using any analytical method for detecting the biomarker in a biological sample and that indicates the presence, absence, absolute amount or concentration, relative amount or concentration, titer, a level, an expression level, a ratio of measured levels, or the like, of, for, or corresponding to the biomarker in the biological sample. The exact nature of the "level" depends on the specific design and components of the particular analytical method employed to detect the biomarker.

A "control level" of a target molecule refers to the level of the target molecule in the same sample type from an individual that does not have the disease or condition, or from an individual that is not suspected of having the disease or condition. A "control level" of a target molecule need not be determined each time the present methods are carried out, and may be a previously determined level that is used as a reference or threshold to determine whether the level in a particular sample is higher or lower than a normal level. In some embodiments, a control level in a method described herein is the level that has been observed in one or more subjects without NAFLD. In some embodiments, a control level in a method described herein is the level that has been observed in one or more subjects with NAFLD, but not NASH. In some embodiments, a control level in a method described herein is the average or mean level, optionally plus or minus a statistical variation, that has been observed in a plurality of normal subjects, or subjects with NAFLD but not NASH.

As used herein, "individual" and "subject" are used interchangeably to refer to a test subject or patient. The individual can be a mammal or a non-mammal. In various embodiments, the individual is a mammal. A mammalian individual can be a human or non-human. In various embodiments, the individual is a human. A healthy or normal individual is an individual in which the disease or condition of interest (such as NASH) is not detectable by conventional diagnostic methods.

"Diagnose", "diagnosing", "diagnosis", and variations thereof refer to the detection, determination, or recognition of a health status or condition of an individual on the basis of one or more signs, symptoms, data, or other information pertaining to that individual. The health status of an individual can be diagnosed as healthy/normal (i.e., a diagnosis of the absence of a disease or condition) or diagnosed as ill/abnormal (i.e., a diagnosis of the presence, or an assessment of the characteristics, of a disease or condition). The terms "diagnose", "diagnosing", "diagnosis", etc., encompass, with respect to a particular disease or condition, the initial detection of the disease; the characterization or classification of the disease; the detection of the progression, remission, or recurrence of the disease; and the detection of disease response after the administration of a treatment or therapy to the individual. The diagnosis of NAFLD includes distinguishing individuals who have NAFLD from individuals who do not. The diagnosis of NASH includes distinguishing individuals who have NASH from individuals who have steatosis in the liver, but not NASH, and from individuals with no liver disease.

"Prognose", "prognosing", "prognosis", and variations thereof refer to the prediction of a future course of a disease or condition in an individual who has the disease or condition (e.g., predicting patient survival), and such terms encompass the evaluation of disease response after the administration of a treatment or therapy to the individual.

"Evaluate", "evaluating", "evaluation", and variations thereof encompass both "diagnose" and "prognose" and also encompass determinations or predictions about the future course of a disease or condition in an individual who does not have the disease as well as determinations or predictions regarding the likelihood that a disease or condition will recur in an individual who apparently has been cured of the disease. The term "evaluate" also encompasses assessing an individual's response to a therapy, such as, for example, predicting whether an individual is likely to respond favorably to a therapeutic agent or is unlikely to respond to a therapeutic agent (or will experience toxic or other undesirable side effects, for example), selecting a therapeutic agent for administration to an individual, or monitoring or determining an individual's response to a therapy that has been administered to the individual. Thus, "evaluating" NAFLD can include, for example, any of the following: prognosing the future course of NAFLD in an individual; predicting whether NAFLD will progress to NASH; predicting whether a particular stage of NASH will progress to a higher stage of NASH; etc.

As used herein, "detecting" or "determining" with respect to a biomarker level includes the use of both the instrument used to observe and record a signal corresponding to a biomarker level and the material/s required to generate that signal. In various embodiments, the level is detected using any suitable method, including fluorescence, chemiluminescence, surface plasmon resonance, surface acoustic waves, mass spectrometry, infrared spectroscopy, Raman spectroscopy, atomic force microscopy, scanning tunneling microscopy, electrochemical detection methods, nuclear magnetic resonance, quantum dots, and the like.

As used herein, a "subject with NAFLD" refers to a subject that has been diagnosed with NAFLD. In some embodiments, NAFLD is suspected during a routine checkup, monitoring of metabolic syndrome and obesity, or monitoring for possible side effects of drugs (e.g., cholesterol lowering agents or steroids). In some instance, liver enzymes such AST and ALT are high. In some embodiments, a subject is diagnosed following abdominal or thoracic imaging, liver ultrasound, or magnetic resonance imaging. In some embodiments, other conditions such as excess alcohol consumption, hepatitis C, and Wilson's disease have been ruled out prior to an NAFLD diagnosis. In some embodiments, a subject has been diagnosed following a liver biopsy.

As used herein, a "subject with steatosis" and a "subject with non-alcoholic steatosis" are used interchangeably, and refer to a subject that has been diagnosed with steatosis. In some embodiments, steatosis is diagnosed by a method described above for NAFLD in general.

As used herein, a "subject with NASH" refers to a subject that has been diagnosed with NASH. In some embodiments, NASH is diagnosed by a method described above for NAFLD in general. In some embodiments, advanced fibrosis is diagnosed in a patient with NAFLD, for example, according to Gambino R, et. al. *Annals of Medicine* 2011; 43(8): 617-49.

As used herein, a "subject at risk of developing NAFLD" refers to a subject with one or more NAFLD comorbidities, such as obesity, abdominal obesity, metabolic syndrome, cardiovascular disease, and diabetes.

As used herein, a "subject at risk of developing steatosis" refers to a subject that has not been diagnosed as having steatosis, but who has one or more NAFLD comorbidities, such as obesity, abdominal obesity, metabolic syndrome, cardiovascular disease, and diabetes.

As used herein, a "subject at risk of developing NASH" refers to a subject with steatosis who continues to have one or more NAFLD comorbidities, such as obesity, abdominal obesity, metabolic syndrome, cardiovascular disease, and diabetes.

"Solid support" refers herein to any substrate having a surface to which molecules may be attached, directly or indirectly, through either covalent or non-covalent bonds. A "solid support" can have a variety of physical formats, which can include, for example, a membrane; a chip (e.g., a protein chip); a slide (e.g., a glass slide or coverslip); a column; a hollow, solid, semi-solid, pore- or cavity-containing particle, such as, for example, a bead; a gel; a fiber, including a fiber optic material; a matrix; and a sample receptacle. Exemplary sample receptacles include sample wells, tubes, capillaries, vials, and any other vessel, groove or indentation capable of holding a sample. A sample receptacle can be contained on a multi-sample platform, such as a microtiter plate, slide, microfluidics device, and the like. A support can be composed of a natural or synthetic material, an organic or inorganic material. The composition of the solid support on which capture reagents are attached generally depends on the method of attachment (e.g., covalent attachment). Other exemplary receptacles include microdroplets and microfluidic controlled or bulk oil/aqueous emulsions within which assays and related manipulations can occur. Suitable solid supports include, for example, plastics, resins, polysaccharides, silica or silica-based materials, functionalized glass, modified silicon, carbon, metals, inorganic glasses, membranes, nylon, natural fibers (such as, for example, silk, wool and cotton), polymers, and the like. The material composing the solid support can include reactive groups such as, for example, carboxy, amino, or hydroxyl groups, which are used for attachment of the capture reagents. Polymeric solid supports can include, e.g., polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly) vinylidenefluoride, polycarbonate, and polymethylpentene. Suitable solid support particles that can be used include, e.g., encoded particles, such as Luminex®-type encoded particles, magnetic particles, and glass particles.

Exemplary Uses of Biomarkers

In various exemplary embodiments, methods are provided for determining whether a subject has NAFLD. In various embodiments, methods are provided for determining whether a subject has steatosis, which may be mild, moderate, or severe steatosis. In various embodiments, methods are provided for determining whether a subject has NASH, which may be stage 1, 2, 3, or 4 NASH, or which may be stage 2, 3, or 4 NASH. In some embodiments, methods of provided for determining whether a subject with steatosis has NASH, which may be stage 1, 2, 3, or 4 NASH, or which may be stage 2, 3, or 4 NASH. The methods comprise detecting one or more biomarker levels corresponding to one or more biomarkers that are present in the circulation of an individual, such as in serum or plasma, by any number of analytical methods, including any of the analytical methods described herein. These biomarkers are, for example, present at different levels in individuals with NAFLD as compared to normal individuals (wherein normal individuals may be obese individuals). In some embodiments, the biomarkers are present at different levels in individuals with NASH (such as stage 1, 2, 3, or 4 NASH, or stage 2, 3, or 4 NASH) as compared to normal individuals (wherein normal individuals may be obese individuals). In some embodiments, the biomarkers are present at different levels in individuals with NASH (such as stage 1, 2, 3, or 4 NASH, or stage 2, 3, or 4 NASH) as compared to subjects with steatosis, which may be mild, moderate, or severe steatosis, Detection of the differential levels of a biomarker in an individual can be used, for example, to permit the determination of whether an individual has NAFLD (which may be steatosis or NASH), or whether an individual with steatosis has developed NASH. In some embodiments, any of the biomarkers described herein may be used to monitor individuals (such as obese individuals) for development of NAFLD, or to monitor individuals with steatosis for development of NASH.

As an example of the manner in which any of the biomarkers described herein can be used to determine whether a subject has NAFLD, levels of one or more of the described biomarkers in an individual who has not been diagnosed with NAFLD, but has one or more NAFLD comorbidities, may indicate that the individual has developed NAFLD at an earlier stage than would be determined using an invasive test, such as liver biopsy. Because the present methods are non-invasive, they may be used to monitor individuals at risk of developing NAFLD (such as, for example, obese individuals). By detecting NAFLD at an earlier stage, medical intervention may be more effective. Such medical intervention may include, but is not limited to, weight loss, blood sugar control, and alcohol avoidance. In some embodiments, therapeutic agents may be used, such as pioglitazone, vitamin E, and/or metformin. See, e.g., Sanyal et al., 2010, *NEJM*, 362: 1675-1685. In some instances, such early intervention may delay or prevent liver failure and the need for a liver transplant.

Similarly, as a further example of the manner in which the biomarkers described herein can be used to determine whether a subject that has steatosis is developing NASH, levels of one or more of the described biomarkers in an individual with steatosis may indicate that the individual is developing NASH. Because the present methods are non-invasive, individuals with steatosis may be monitored for development of NASH. By detecting NASH at an earlier stage, medical intervention may be more effective. Such medical intervention may include, but is not limited to, weight loss, blood sugar control, and alcohol avoidance. In some embodiments, therapeutic agents may be used, such as pioglitazone, vitamin E, and/or metformin. See, e.g., Sanyal et al., 2010, *NEJM*, 362: 1675-1685. In some instances, such early intervention may delay or prevent liver failure and the need for a liver transplant.

In addition, in some embodiments, a differential expression level of one or more of the biomarkers in an individual over time may be indicative of the individual's response to a particular therapeutic regimen. In some embodiments, changes in expression of one or more of the biomarkers during follow-up monitoring may indicate that a particular therapy is effective or may suggest that the therapeutic regimen should be altered in some way, such as by more aggressively controlling blood sugar, more aggressively pursuing weight loss, etc. In some embodiments, a constant expression level of one or more of the biomarkers in an individual over time may be indicative that an individual's steatosis is not worsening, or is not developing into NASH.

In addition to testing biomarker levels as a stand-alone diagnostic test, biomarker levels can also be done in conjunction with determination of single nucleotide polymorphisms (SNPs) or other genetic lesions or variability that are indicative of increased risk of susceptibility of disease. (See, e.g., Amos et al., Nature Genetics 40, 616-622 (2009)).

In addition to testing biomarker levels as a stand-alone diagnostic test, biomarker levels can also be done in conjunction with other NAFLD screening methods, such as detection of an enlarged liver, blood tests (for example, to detect elevations in certain liver enzymes, such as ALT and/or AST), abdominal ultrasound, and liver biopsy. In some instances, methods using the biomarkers described herein may facilitate the medical and economic justification for implementing more aggressive treatments for NAFLD or NASH, more frequent follow-up screening, etc. The biomarkers may also be used to begin treatment in individuals at risk of developing NAFLD, but who have not been diagnosed with steatosis, if the diagnostic test indicates they are likely to develop the disease.

In addition to testing biomarker levels in conjunction with other NAFLD diagnostic methods, information regarding the biomarkers can also be evaluated in conjunction with other types of data, particularly data that indicates an individual's risk for NAFLD. These various data can be assessed by automated methods, such as a computer program/software, which can be embodied in a computer or other apparatus/device.

Detection and Determination of Biomarkers and Biomarker Levels

A biomarker level for the biomarkers described herein can be detected using any of a variety of known analytical methods. In one embodiment, a biomarker level is detected using a capture reagent. In various embodiments, the capture reagent can be exposed to the biomarker in solution or can be exposed to the biomarker while the capture reagent is immobilized on a solid support. In other embodiments, the capture reagent contains a feature that is reactive with a secondary feature on a solid support. In these embodiments, the capture reagent can be exposed to the biomarker in solution, and then the feature on the capture reagent can be used in conjunction with the secondary feature on the solid support to immobilize the biomarker on the solid support. The capture reagent is selected based on the type of analysis to be conducted. Capture reagents include but are not limited to aptamers, antibodies, adnectins, ankyrins, other antibody mimetics and other protein scaffolds, autoantibodies, chimeras, small molecules, F(ab')2 fragments, single chain antibody fragments, Fv fragments, single chain Fv fragments, nucleic acids, lectins, ligand-binding receptors, affybodies, nanobodies, imprinted polymers, avimers, peptidomimetics, hormone receptors, cytokine receptors, and synthetic receptors, and modifications and fragments of these.

In some embodiments, a biomarker level is detected using a biomarker/capture reagent complex.

In some embodiments, the biomarker level is derived from the biomarker/capture reagent complex and is detected indirectly, such as, for example, as a result of a reaction that is subsequent to the biomarker/capture reagent interaction, but is dependent on the formation of the biomarker/capture reagent complex.

In some embodiments, the biomarker level is detected directly from the biomarker in a biological sample.

In some embodiments, biomarkers are detected using a multiplexed format that allows for the simultaneous detection of two or more biomarkers in a biological sample. In some embodiments of the multiplexed format, capture reagents are immobilized, directly or indirectly, covalently or non-covalently, in discrete locations on a solid support. In some embodiments, a multiplexed format uses discrete solid supports where each solid support has a unique capture reagent associated with that solid support, such as, for example quantum dots. In some embodiments, an individual device is used for the detection of each one of multiple biomarkers to be detected in a biological sample. Individual devices can be configured to permit each biomarker in the biological sample to be processed simultaneously. For example, a microtiter plate can be used such that each well in the plate is used to analyze one or more of multiple biomarkers to be detected in a biological sample.

In one or more of the foregoing embodiments, a fluorescent tag can be used to label a component of the biomarker/capture reagent complex to enable the detection of the biomarker level. In various embodiments, the fluorescent label can be conjugated to a capture reagent specific to any of the biomarkers described herein using known techniques, and the fluorescent label can then be used to detect the corresponding biomarker level. Suitable fluorescent labels include rare earth chelates, fluorescein and its derivatives, rhodamine and its derivatives, dansyl, allophycocyanin, PBXL-3, QDOT 605, Lissamine, phycoerythrin, TEXAS RED, and other such compounds.

In some embodiments, the fluorescent label is a fluorescent dye molecule. In some embodiments, the fluorescent dye molecule includes at least one substituted indolium ring system in which the substituent on the 3-carbon of the indolium ring contains a chemically reactive group or a conjugated substance. In some embodiments, the dye molecule includes an AlexFluor molecule, such as, for example, AlexaFluor 488, AlexaFluor 532, AlexaFluor 647, AlexaFluor 680, or AlexaFluor 700. In some embodiments, the dye molecule includes a first type and a second type of dye molecule, such as, e.g., two different AlexaFluor molecules. In some embodiments, the dye molecule includes a first type and a second type of dye molecule, and the two dye molecules have different emission spectra.

Fluorescence can be measured with a variety of instrumentation compatible with a wide range of assay formats. For example, spectrofluorimeters have been designed to analyze microtiter plates, microscope slides, printed arrays, cuvettes, etc. See Principles of Fluorescence Spectroscopy, by J. R. Lakowicz, Springer Science+Business Media, Inc., 2004. See Bioluminescence & Chemiluminescence: Progress & Current Applications; Philip E. Stanley and Larry J. Kricka editors, World Scientific Publishing Company, January 2002.

In one or more embodiments, a chemiluminescence tag can optionally be used to label a component of the biomarker/capture complex to enable the detection of a biomarker level. Suitable chemiluminescent materials include any of oxalyl chloride, Rodamin 6G, $Ru(bipy)_3^{2+}$, TMAE (tetrakis(dimethylamino)ethylene), Pyrogallol (1,2,3-trihydroxibenzene), Lucigenin, peroxyoxalates, Aryl oxalates, Acridinium esters, dioxetanes, and others.

In some embodiments, the detection method includes an enzyme/substrate combination that generates a detectable signal that corresponds to the biomarker level. Generally, the enzyme catalyzes a chemical alteration of the chromogenic substrate which can be measured using various techniques, including spectrophotometry, fluorescence, and chemiluminescence. Suitable enzymes include, for example, luciferases, luciferin, malate dehydrogenase, urease, horseradish peroxidase (HRPO), alkaline phosphatase, beta-galactosidase, glucoamylase, lysozyme, glucose oxidase, galactose oxidase, and glucose-6-phosphate dehydrogenase, uricase, xanthine oxidase, lactoperoxidase, microperoxidase, and the like.

In some embodiments, the detection method can be a combination of fluorescence, chemiluminescence, radionuclide or enzyme/substrate combinations that generate a measurable signal. In some embodiments, multimodal signaling could have unique and advantageous characteristics in biomarker assay formats.

In some embodiments, the biomarker levels for the biomarkers described herein can be detected using any analytical methods including, singleplex aptamer assays, multiplexed aptamer assays, singleplex or multiplexed immunoassays, mRNA expression profiling, miRNA expression profiling, mass spectrometric analysis, histological/cytological methods, etc. as discussed below.

Determination of Biomarker Levels Using Aptamer-Based Assays

Assays directed to the detection and quantification of physiologically significant molecules in biological samples and other samples are important tools in scientific research and in the health care field. One class of such assays involves the use of a microarray that includes one or more aptamers immobilized on a solid support. The aptamers are each capable of binding to a target molecule in a highly specific manner and with very high affinity. See, e.g., U.S. Pat. No. 5,475,096 entitled "Nucleic Acid Ligands"; see also, e.g., U.S. Pat. Nos. 6,242,246, 6,458,543, and 6,503,715, each of which is entitled "Nucleic Acid Ligand Diagnostic Biochip". Once the microarray is contacted with a sample, the aptamers bind to their respective target molecules present in the sample and thereby enable a determination of a biomarker level corresponding to a biomarker.

As used herein, an "aptamer" refers to a nucleic acid that has a specific binding affinity for a target molecule. It is recognized that affinity interactions are a matter of degree; however, in this context, the "specific binding affinity" of an aptamer for its target means that the aptamer binds to its target generally with a much higher degree of affinity than it binds to other components in a test sample. An "aptamer" is a set of copies of one type or species of nucleic acid molecule that has a particular nucleotide sequence. An aptamer can include any suitable number of nucleotides, including any number of chemically modified nucleotides. "Aptamers" refers to more than one such set of molecules. Different aptamers can have either the same or different numbers of nucleotides. Aptamers can be DNA or RNA or chemically modified nucleic acids and can be single stranded, double stranded, or contain double stranded regions, and can include higher ordered structures. An aptamer can also be a photoaptamer, where a photoreactive or chemically reactive functional group is included in the aptamer to allow it to be covalently linked to its corresponding target. Any of the aptamer methods disclosed herein can include the use of two or more aptamers that specifically bind the same target molecule. As further described below, an aptamer may include a tag. If an aptamer includes a tag, all copies of the aptamer need not have the same tag. Moreover, if different aptamers each include a tag, these different aptamers can have either the same tag or a different tag.

An aptamer can be identified using any known method, including the SELEX process. Once identified, an aptamer can be prepared or synthesized in accordance with any known method, including chemical synthetic methods and enzymatic synthetic methods.

The terms "SELEX" and "SELEX process" are used interchangeably herein to refer generally to a combination of (1) the selection of aptamers that interact with a target molecule in a desirable manner, for example binding with high affinity to a protein, with (2) the amplification of those selected nucleic acids. The SELEX process can be used to identify aptamers with high affinity to a specific target or biomarker.

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands". The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides", which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH2), 2'-fluoro (2'-F), and/or 2'-O-methyl (2'-OMe). See also, U.S. Patent Application Publication No. 2009/0098549, entitled "SELEX and PHOTOSELEX", which describes nucleic acid libraries having expanded physical and chemical properties and their use in SELEX and photoSELEX.

Figure 11:
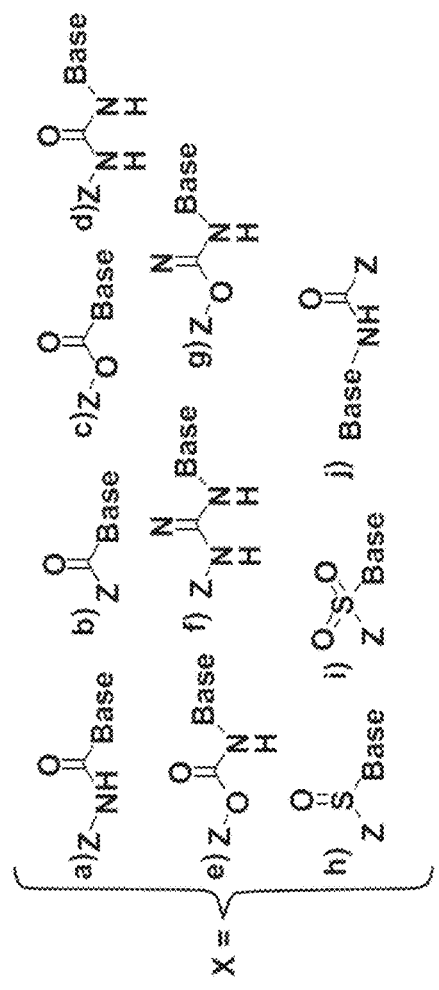
FIG. 11 shows certain exemplary modified pyrimidines that may be incorporated into aptamers, such as slow off-rate aptamers.
Figure 11:
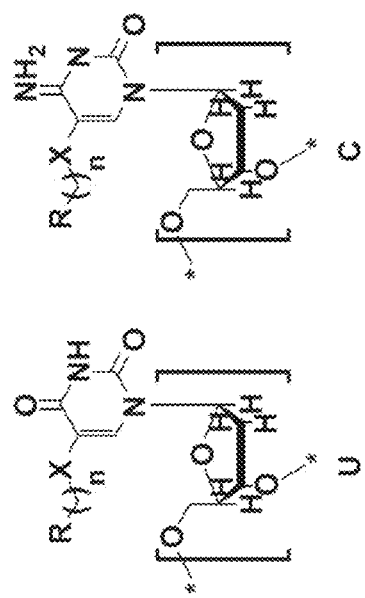
Figure 11:
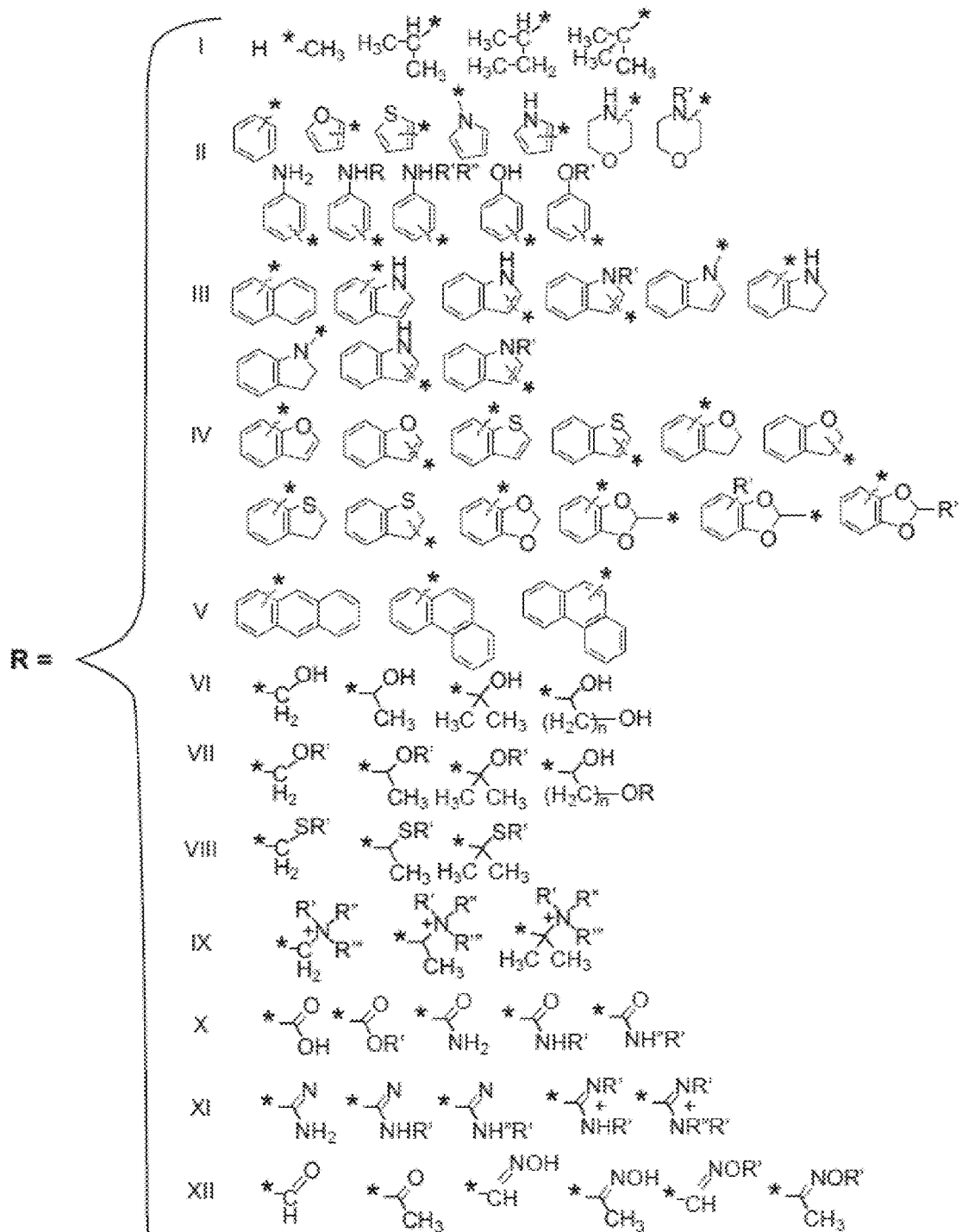

SELEX can also be used to identify aptamers that have desirable off-rate characteristics. See U.S. Publication No. US 2009/0004667, entitled "Method for Generating Aptamers with Improved Off-Rates", which describes improved SELEX methods for generating aptamers that can bind to target molecules. Methods for producing aptamers and photoaptamers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates will dissociate and not reform, while complexes with slow dissociation rates will remain intact. Additionally, the methods include the use of modified nucleotides in the production of candidate nucleic acid mixtures to generate aptamers with improved off-rate performance. Nonlimiting exemplary modified nucleotides include, for example, the modified pyrimidines shown in FIG. 11. In some embodiments, an aptamer comprises at least one nucleotide with a modification, such as a base modification. In some embodiments, an aptamer comprises at least one nucleotide with a hydrophobic modification, such as a hydrophobic base modification, allowing for hydrophobic contacts with a target protein. Such hydrophobic contacts, in some embodiments, contribute to greater affinity and/or slower off-rate binding by the aptamer. Nonlimiting exemplary nucleotides with hydrophobic modifications are shown in FIG. 11. In some embodiments, an aptamer comprises at least two, at least three, at least four, at least five, at least six, at least seven, at least eight, at least nine, or at least 10 nucleotides with hydrophobic modifications, where each hydrophobic modification may be the same or different from the others. In some embodiments, at least one, at least two, at least three, at least four, at least five, at least six, at least seven, at least eight, at least nine, or at least 10 hydrophobic modifications in an aptamer may be independently selected from the hydrophobic modifications shown in FIG. 11.

In some embodiments, a slow off-rate aptamer (including an aptamers comprising at least one nucleotide with a hydrophobic modification) has an off-rate (t½) of ≥30 minutes, ≥60 minutes, ≥90 minutes, ≥120 minutes, ≥150 minutes, ≥180 minutes, ≥210 minutes, or ≥240 minutes.

In some embodiments, an assay employs aptamers that include photoreactive functional groups that enable the aptamers to covalently bind or "photocrosslink" their target molecules. See, e.g., U.S. Pat. No. 6,544,776 entitled "Nucleic Acid Ligand Diagnostic Biochip". These photoreactive aptamers are also referred to as photoaptamers. See, e.g., U.S. Pat. Nos. 5,763,177, 6,001,577, and 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands". After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds created by the photoactivated functional group(s) on the photoaptamers. In this manner, the assay enables the detection of a biomarker level corresponding to a biomarker in the test sample.

In some assay formats, the aptamers are immobilized on the solid support prior to being contacted with the sample. Under certain circumstances, however, immobilization of the aptamers prior to contact with the sample may not provide an optimal assay. For example, pre-immobilization of the aptamers may result in inefficient mixing of the aptamers with the target molecules on the surface of the solid support, perhaps leading to lengthy reaction times and, therefore, extended incubation periods to permit efficient binding of the aptamers to their target molecules. Further, when photoaptamers are employed in the assay and depending upon the material utilized as a solid support, the solid support may tend to scatter or absorb the light used to effect the formation of covalent bonds between the photoaptamers and their target molecules. Moreover, depending upon the method employed, detection of target molecules bound to their aptamers can be subject to imprecision, since the surface of the solid support may also be exposed to and affected by any labeling agents that are used. Finally, immobilization of the aptamers on the solid support generally involves an aptamer-preparation step (i.e., the immobilization) prior to exposure of the aptamers to the sample, and this preparation step may affect the activity or functionality of the aptamers.

Aptamer assays that permit an aptamer to capture its target in solution and then employ separation steps that are designed to remove specific components of the aptamer-target mixture prior to detection have also been described (see U.S. Publication No. 2009/0042206, entitled "Multiplexed Analyses of Test Samples"). The described aptamer assay methods enable the detection and quantification of a non-nucleic acid target (e.g., a protein target) in a test sample by detecting and quantifying a nucleic acid (i.e., an aptamer). The described methods create a nucleic acid surrogate (i.e, the aptamer) for detecting and quantifying a non-nucleic acid target, thus allowing the wide variety of nucleic acid technologies, including amplification, to be applied to a broader range of desired targets, including protein targets.

Aptamers can be constructed to facilitate the separation of the assay components from an aptamer biomarker complex (or photoaptamer biomarker covalent complex) and permit isolation of the aptamer for detection and/or quantification. In one embodiment, these constructs can include a cleavable or releasable element within the aptamer sequence. In other embodiments, additional functionality can be introduced into the aptamer, for example, a labeled or detectable component, a spacer component, or a specific binding tag or immobilization element. For example, the aptamer can include a tag connected to the aptamer via a cleavable moiety, a label, a spacer component separating the label, and the cleavable moiety. In one embodiment, a cleavable element is a photocleavable linker. The photocleavable linker can be attached to a biotin moiety and a spacer section, can include an NHS group for derivatization of amines, and can be used to introduce a biotin group to an aptamer, thereby allowing for the release of the aptamer later in an assay method.

Homogenous assays, done with all assay components in solution, do not require separation of sample and reagents prior to the detection of signal. These methods are rapid and easy to use. These methods generate signal based on a molecular capture or binding reagent that reacts with its specific target. In some embodiments of the methods described herein, the molecular capture reagents comprise an aptamer or an antibody or the like and the specific target may be a biomarker shown in Table 3, 4, 6, or 7.

In some embodiments, a method for signal generation takes advantage of anisotropy signal change due to the interaction of a fluorophore-labeled capture reagent with its specific biomarker target. When the labeled capture reacts with its target, the increased molecular weight causes the rotational motion of the fluorophore attached to the complex to become much slower changing the anisotropy value. By monitoring the anisotropy change, binding events may be used to quantitatively measure the biomarkers in solutions. Other methods include fluorescence polarization assays, molecular beacon methods, time resolved fluorescence quenching, chemiluminescence, fluorescence resonance energy transfer, and the like.

An exemplary solution-based aptamer assay that can be used to detect a biomarker level in a biological sample includes the following: (a) preparing a mixture by contacting the biological sample with an aptamer that includes a first tag and has a specific affinity for the biomarker, wherein an aptamer affinity complex is formed when the biomarker is present in the sample; (b) exposing the mixture to a first solid support including a first capture element, and allowing the first tag to associate with the first capture element; (c) removing any components of the mixture not associated with the first solid support; (d) attaching a second tag to the biomarker component of the aptamer affinity complex; (e) releasing the aptamer affinity complex from the first solid support; (f) exposing the released aptamer affinity complex to a second solid support that includes a second capture element and allowing the second tag to associate with the second capture element; (g) removing any non-complexed aptamer from the mixture by partitioning the non-complexed aptamer from the aptamer affinity complex; (h) eluting the aptamer from the solid support; and (i) detecting the biomarker by detecting the aptamer component of the aptamer affinity complex.

A nonlimiting exemplary method of detecting biomarkers in a biological sample using aptamers is described in Example 7. See also Kraemer et al., *PLoS One* 6(10): e26332.

Determination of Biomarker Levels Using Immunoassays

Immunoassay methods are based on the reaction of an antibody to its corresponding target or analyte and can detect the analyte in a sample depending on the specific assay format. To improve specificity and sensitivity of an assay method based on immuno-reactivity, monoclonal antibodies and fragments thereof are often used because of their specific epitope recognition. Polyclonal antibodies have also been successfully used in various immunoassays because of their increased affinity for the target as compared to monoclonal antibodies. Immunoassays have been designed for use with a wide range of biological sample matrices. Immunoassay formats have been designed to provide qualitative, semi-quantitative, and quantitative results.

Quantitative results are generated through the use of a standard curve created with known concentrations of the specific analyte to be detected. The response or signal from an unknown sample is plotted onto the standard curve, and a quantity or level corresponding to the target in the unknown sample is established.

Numerous immunoassay formats have been designed. ELISA or EIA can be quantitative for the detection of an analyte. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or for quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 386 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Determination of Biomarker Levels Using Gene Expression Profiling

Measuring mRNA in a biological sample may, in some embodiments, be used as a surrogate for detection of the level of the corresponding protein in the biological sample. Thus, in some embodiments, a biomarker or biomarker panel described herein can be detected by detecting the appropriate RNA.

In some embodiments, mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

Detection of Biomarkers Using In Vivo Molecular Imaging Technologies

In some embodiments, a biomarker described herein may be used in molecular imaging tests. For example, an imaging agent can be coupled to a capture reagent, which can be used to detect the biomarker in vivo.

In vivo imaging technologies provide non-invasive methods for determining the state of a particular disease in the body of an individual. For example, entire portions of the body, or even the entire body, may be viewed as a three dimensional image, thereby providing valuable information concerning morphology and structures in the body. Such technologies may be combined with the detection of the biomarkers described herein to provide information concerning the biomarker in vivo.

The use of in vivo molecular imaging technologies is expanding due to various advances in technology. These advances include the development of new contrast agents or labels, such as radiolabels and/or fluorescent labels, which can provide strong signals within the body; and the development of powerful new imaging technology, which can detect and analyze these signals from outside the body, with sufficient sensitivity and accuracy to provide useful information. The contrast agent can be visualized in an appropriate imaging system, thereby providing an image of the portion or portions of the body in which the contrast agent is located. The contrast agent may be bound to or associated with a capture reagent, such as an aptamer or an antibody, for example, and/or with a peptide or protein, or an oligonucleotide (for example, for the detection of gene expression), or a complex containing any of these with one or more macromolecules and/or other particulate forms.

The contrast agent may also feature a radioactive atom that is useful in imaging. Suitable radioactive atoms include technetium-99m or iodine-123 for scintigraphic studies. Other readily detectable moieties include, for example, spin labels for magnetic resonance imaging (MRI) such as, for example, iodine-123 again, iodine-131, indium-111, fluorine-19, carbon-13, nitrogen-15, oxygen-17, gadolinium, manganese or iron. Such labels are well known in the art and could easily be selected by one of ordinary skill in the art.

Standard imaging techniques include but are not limited to magnetic resonance imaging, computed tomography scanning, positron emission tomography (PET), single photon emission computed tomography (SPECT), and the like. For diagnostic in vivo imaging, the type of detection instrument available is a major factor in selecting a given contrast agent, such as a given radionuclide and the particular biomarker that it is used to target (protein, mRNA, and the like). The radionuclide chosen typically has a type of decay that is detectable by a given type of instrument. Also, when selecting a radionuclide for in vivo diagnosis, its half-life should be long enough to enable detection at the time of maximum uptake by the target tissue but short enough that deleterious radiation of the host is minimized.

Exemplary imaging techniques include but are not limited to PET and SPECT, which are imaging techniques in which a radionuclide is synthetically or locally administered to an individual. The subsequent uptake of the radiotracer is measured over time and used to obtain information about the targeted tissue and the biomarker. Because of the high-energy (gamma-ray) emissions of the specific isotopes employed and the sensitivity and sophistication of the instruments used to detect them, the two-dimensional distribution of radioactivity may be inferred from outside of the body.

Commonly used positron-emitting nuclides in PET include, for example, carbon-11, nitrogen-13, oxygen-15, and fluorine-18. Isotopes that decay by electron capture and/or gamma-emission are used in SPECT and include, for example iodine-123 and technetium-99m. An exemplary method for labeling amino acids with technetium-99m is the reduction of pertechnetate ion in the presence of a chelating precursor to form the labile technetium-99m-precursor complex, which, in turn, reacts with the metal binding group of a bifunctionally modified chemotactic peptide to form a technetium-99m-chemotactic peptide conjugate.

Antibodies are frequently used for such in vivo imaging diagnostic methods. The preparation and use of antibodies for in vivo diagnosis is well known in the art. Similarly, aptamers may be used for such in vivo imaging diagnostic methods. For example, an aptamer that was used to identify a particular biomarker described herein may be appropriately labeled and injected into an individual to detect the biomarker in vivo. The label used will be selected in accordance with the imaging modality to be used, as previously described. Aptamer-directed imaging agents could have unique and advantageous characteristics relating to tissue penetration, tissue distribution, kinetics, elimination, potency, and selectivity as compared to other imaging agents.

Such techniques may also optionally be performed with labeled oligonucleotides, for example, for detection of gene expression through imaging with antisense oligonucleotides. These methods are used for in situ hybridization, for example, with fluorescent molecules or radionuclides as the label. Other methods for detection of gene expression include, for example, detection of the activity of a reporter gene.

Another general type of imaging technology is optical imaging, in which fluorescent signals within the subject are detected by an optical device that is external to the subject. These signals may be due to actual fluorescence and/or to bioluminescence. Improvements in the sensitivity of optical detection devices have increased the usefulness of optical imaging for in vivo diagnostic assays.

For a review of other techniques, see N. Blow, Nature Methods, 6, 465-469, 2009.

Determination of Biomarkers Using Histology/Cytology Methods

In some embodiments, the biomarkers described herein may be detected in a variety of tissue samples using histological or cytological methods. For example, endo- and trans-bronchial biopsies, fine needle aspirates, cutting needles, and core biopsies can be used for histology. Bronchial washing and brushing, pleural aspiration, and sputum, can be used for cyotology. Any of the biomarkers identified herein can be used to stain a specimen as an indication of disease.

In some embodiments, one or more capture reagent/s specific to the corresponding biomarker/s are used in a cytological evaluation of a sample and may include one or more of the following: collecting a cell sample, fixing the cell sample, dehydrating, clearing, immobilizing the cell sample on a microscope slide, permeabilizing the cell sample, treating for analyte retrieval, staining, destaining, washing, blocking, and reacting with one or more capture reagent/s in a buffered solution. In another embodiment, the cell sample is produced from a cell block.

In some embodiments, one or more capture reagent/s specific to the corresponding biomarkers are used in a histological evaluation of a tissue sample and may include one or more of the following: collecting a tissue specimen, fixing the tissue sample, dehydrating, clearing, immobilizing the tissue sample on a microscope slide, permeabilizing the tissue sample, treating for analyte retrieval, staining, destaining, washing, blocking, rehydrating, and reacting with capture reagent/s in a buffered solution. In another embodiment, fixing and dehydrating are replaced with freezing.

In another embodiment, the one or more aptamer/s specific to the corresponding biomarker/s are reacted with the histological or cytological sample and can serve as the nucleic acid target in a nucleic acid amplification method. Suitable nucleic acid amplification methods include, for example, PCR, q-beta replicase, rolling circle amplification, strand displacement, helicase dependent amplification, loop mediated isothermal amplification, ligase chain reaction, and restriction and circularization aided rolling circle amplification.

In one embodiment, the one or more capture reagent/s specific to the corresponding biomarkers for use in the histological or cytological evaluation are mixed in a buffered solution that can include any of the following: blocking materials, competitors, detergents, stabilizers, carrier nucleic acid, polyanionic materials, etc.

A "cytology protocol" generally includes sample collection, sample fixation, sample immobilization, and staining. "Cell preparation" can include several processing steps after sample collection, including the use of one or more aptamers for the staining of the prepared cells.

Determination of Biomarker Levels using Mass Spectrometry Methods

A variety of configurations of mass spectrometers can be used to detect biomarker levels. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al. Anal. Chem. 70:647 R-716R (1998); Kinter and Sherman, New York (2000)).

Protein biomarkers and biomarker levels can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-$(MS)^N$, atmospheric pressure photoionization mass spectrometry (APPI-MS), APPI-MS/MS, and APPI-$(MS)^N$, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker levels. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')$_2$ fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

The foregoing assays enable the detection of biomarker levels that are useful in the methods described herein, where the methods comprise detecting, in a biological sample from an individual, at least one, at least two, at least three, at least four, at least five, at least six, at least seven, at least eight, or at least nine biomarkers selected from the biomarkers in Tables 3, 4, 6, and 7. In various embodiments, the methods comprise detecting the levels of one or more biomarkers selected from any of the groups of biomarkers described herein, such as the panels shown in Table 5 and subsets of the biomarkers shown in Tables 3, 4, 6, and 7. Thus, while some of the described biomarkers may be useful alone for detecting NAFLD and/or NASH, methods are also described herein for the grouping of multiple biomarkers and subsets of the biomarkers to form panels of two or more biomarkers. In accordance with any of the methods described herein, biomarker levels can be detected and classified individually or they can be detected and classified collectively, as for example in a multiplex assay format.

Classification of Biomarkers and Calculation of Disease Scores

In some embodiments, a biomarker "signature" for a given diagnostic test contains a set of biomarkers, each biomarker having characteristic levels in the populations of interest. Characteristic levels, in some embodiments, may refer to the mean or average of the biomarker levels for the individuals in a particular group. In some embodiments, a diagnostic method described herein can be used to assign an unknown sample from an individual into one of two groups, either NAFLD or normal. In some embodiments, a diagnostic method described herein can be used to assign an unknown sample from an individual into one of two groups, either NASH or NAFLD. In some embodiments, a diagnostic method described herein can be used to assign an unknown sample from an individual into one of three groups: normal, NAFLD without NASH, and NASH.

The assignment of a sample into one of two or more groups is known as classification, and the procedure used to accomplish this assignment is known as a classifier or a classification method. Classification methods may also be referred to as scoring methods. There are many classification methods that can be used to construct a diagnostic classifier from a set of biomarker levels. In some instances, classification methods are performed using supervised learning techniques in which a data set is collected using samples obtained from individuals within two (or more, for multiple classification states) distinct groups one wishes to distinguish. Since the class (group or population) to which each sample belongs is known in advance for each sample, the classification method can be trained to give the desired classification response. It is also possible to use unsupervised learning techniques to produce a diagnostic classifier.

Common approaches for developing diagnostic classifiers include decision trees; bagging+boosting+forests; rule inference based learning; Parzen Windows; linear models; logistic; neural network methods; unsupervised clustering; K-means; hierarchical ascending/descending; semi-supervised learning; prototype methods; nearest neighbor; kernel density estimation; support vector machines; hidden Markov models; Boltzmann Learning; and classifiers may be combined either simply or in ways which minimize particular objective functions. For a review, see, e.g., Pattern Classification, R. O. Duda, et al., editors, John Wiley & Sons, 2nd edition, 2001; see also, The Elements of Statistical Learning—Data Mining, Inference, and Prediction, T. Hastie, et al., editors, Springer Science+Business Media, LLC, 2nd edition, 2009.

To produce a classifier using supervised learning techniques, a set of samples called training data are obtained. In the context of diagnostic tests, training data includes samples from the distinct groups (classes) to which unknown samples will later be assigned. For example, samples collected from individuals in a control population and individuals in a particular disease population can constitute training data to develop a classifier that can classify unknown samples (or, more particularly, the individuals from whom the samples were obtained) as either having the disease or being free from the disease. The development of the classifier from the training data is known as training the classifier. Specific details on classifier training depend on the nature of the supervised learning technique. Training a naïve Bayesian classifier is an example of such a supervised learning technique (see, e.g., Pattern Classification, R. O. Duda, et al., editors, John Wiley & Sons, 2nd edition, 2001; see also, The Elements of Statistical Learning—Data Mining, Inference, and Prediction, T. Hastie, et al., editors, Springer Science+Business Media, LLC, 2nd edition, 2009). Training of a naïve Bayesian classifier is described, e.g., in U.S. Publication Nos: 2012/0101002 and 2012/0077695.

Since typically there are many more potential biomarker levels than samples in a training set, care must be used to avoid over-fitting. Over-fitting occurs when a statistical model describes random error or noise instead of the underlying relationship. Over-fitting can be avoided in a variety of way, including, for example, by limiting the number of biomarkers used in developing the classifier, by assuming that the biomarker responses are independent of one another, by limiting the complexity of the underlying statistical model employed, and by ensuring that the underlying statistical model conforms to the data.

An illustrative example of the development of a diagnostic test using a set of biomarkers includes the application of a naïve Bayes classifier, a simple probabilistic classifier based on Bayes theorem with strict independent treatment of the biomarkers. Each biomarker is described by a class-dependent probability density function (pdf) for the measured RFU values or log RFU (relative fluorescence units) values in each class. The joint pdfs for the set of biomarkers in one class is assumed to be the product of the individual class-dependent pdfs for each biomarker. Training a naïve Bayes classifier in this context amounts to assigning parameters ("parameterization") to characterize the class dependent pdfs. Any underlying model for the class-dependent pdfs may be used, but the model should generally conform to the data observed in the training set.

The performance of the naïve Bayes classifier is dependent upon the number and quality of the biomarkers used to construct and train the classifier. A single biomarker will perform in accordance with its KS-distance (Kolmogorov-Smirnov). The addition of subsequent biomarkers with good KS distances (>0.3, for example) will, in general, improve the classification performance if the subsequently added biomarkers are independent of the first biomarker. Using the sensitivity plus specificity as a classifier score, many high scoring classifiers can be generated with a variation of a greedy algorithm. (A greedy algorithm is any algorithm that follows the problem solving metaheuristic of making the locally optimal choice at each stage with the hope of finding the global optimum.)

Another way to depict classifier performance is through a receiver operating characteristic (ROC), or simply ROC curve or ROC plot. The ROC is a graphical plot of the sensitivity, or true positive rate, vs. false positive rate (1—specificity or 1—true negative rate), for a binary classifier system as its discrimination threshold is varied. The ROC can also be represented equivalently by plotting the fraction of true positives out of the positives (TPR=true positive rate) vs. the fraction of false positives out of the negatives (FPR=false positive rate). Also known as a Relative Operating Characteristic curve, because it is a comparison of two operating characteristics (TPR & FPR) as the criterion changes. The area under the ROC curve (AUC) is commonly used as a summary measure of diagnostic accuracy. It can take values from 0.0 to 1.0. The AUC has an important statistical property: the AUC of a classifier is equivalent to the probability that the classifier will rank a randomly chosen positive instance higher than a randomly chosen negative instance (Fawcett T, 2006. An introduction to ROC analysis. Pattern Recognition Letters 0.27: 861-874). This is equivalent to the Wilcoxon test of ranks (Hanley, J. A., McNeil, B. J., 1982. The meaning and use of the area under a receiver operating characteristic (ROC) curve. Radiology 143, 29-36.).

Exemplary embodiments use any number of the biomarkers listed in Tables 3, 4, 6, and 7 in various combinations to produce diagnostic tests for identifying individuals with NAFLD. The biomarkers listed in Tables 3, 4, 6, and 7 can be combined in many ways to produce classifiers. In some embodiments, panels of biomarkers are comprised of different sets of biomarkers depending on a specific diagnostic performance criterion that is selected. For example, certain combinations of biomarkers may produce tests that are more sensitive (or more specific) than other combinations. In some embodiments, a panel of biomarkers for identifying individuals with NAFLD is selected from the panels in Table 5.

Exemplary embodiments use any number of the biomarkers listed in Tables 3, 4, 6, and 7 in various combinations to produce diagnostic tests for identifying individuals with steatosis. The biomarkers listed in Tables 3, 4, 6, and 7 can be combined in many ways to produce classifiers. In some embodiments, panels of biomarkers are comprised of different sets of biomarkers depending on a specific diagnostic performance criterion that is selected. For example, certain combinations of biomarkers may produce tests that are more sensitive (or more specific) than other combinations. In some embodiments, a panel of biomarkers for identifying individuals with steatosis is selected from the panels in Table 5. In some embodiments, a panel of biomarkers for identifying individuals with steatosis comprises the biomarkers in Table 3.

Exemplary embodiments use any number of the biomarkers listed in Tables 3, 4, 6, and 7 in various combinations to produce diagnostic tests for identifying individuals with NASH. The biomarkers listed in Tables 3, 4, 6, and 7 can be combined in many ways to produce classifiers. In some embodiments, panels of biomarkers are comprised of different sets of biomarkers depending on a specific diagnostic performance criterion that is selected. For example, certain combinations of biomarkers may produce tests that are more sensitive (or more specific) than other combinations. In some embodiments, a panel of biomarkers for identifying individuals with NASH is selected from the panels in Table 5. In some embodiments, a panel of biomarkers for identifying individuals with NASH comprises the biomarkers in Table 4.

Exemplary embodiments use any number of the biomarkers listed in Tables 3, 4, 6, and 7 in various combinations to produce diagnostic tests for identifying individuals with NAFLD, steatosis, and/or NASH. The biomarkers listed in Tables 3, 4, 6, and 7 can be combined in many ways to produce classifiers. In some embodiments, panels of biomarkers are comprised of different sets of biomarkers depending on a specific diagnostic performance criterion that is selected. For example, certain combinations of biomarkers may produce tests that are more sensitive (or more specific) than other combinations. In some embodiments, a panel of biomarkers for identifying individuals with NAFLD, steatosis, and/or NASH is selected from the panels in Table 5.

In some embodiments, once a panel is defined to include a particular set of biomarkers from Tables 3, 4, 6, and 7 and a classifier is constructed from a set of training data, the diagnostic test parameters are complete. In some embodiments, a biological sample is run in one or more assays to produce the relevant quantitative biomarker levels used for classification. The measured biomarker levels are used as input for the classification method that outputs a classification and an optional score for the sample that reflects the confidence of the class assignment.

In some embodiments, a biological sample is optionally diluted and run in a multiplexed aptamer assay, and data is assessed as follows. First, the data from the assay are optionally normalized and calibrated, and the resulting biomarker levels are used as input to a Bayes classification scheme. Second, the log-likelihood ratio is computed for each measured biomarker individually and then summed to produce a final classification score, which is also referred to as a diagnostic score. The resulting assignment as well as the overall classification score can be reported. In some embodiments, the individual log-likelihood risk factors computed for each biomarker level can be reported as well.

Kits

Any combination of the biomarkers described herein can be detected using a suitable kit, such as for use in performing the methods disclosed herein. Furthermore, any kit can contain one or more detectable labels as described herein, such as a fluorescent moiety, etc.

In some embodiments, a kit includes (a) one or more capture reagents (such as, for example, at least one aptamer or antibody) for detecting one or more biomarkers in a biological sample, and optionally (b) one or more software or computer program products for predicting whether the individual from whom the biological sample was obtained has NAFLD, steatosis, and/or NASH (such as stage 1, 2, 3, or 4 NASH, or stage 2, 3, or 4 NASH). Alternatively, rather than one or more computer program products, one or more instructions for manually performing the above steps by a human can be provided.

In some embodiments, a kit comprises a solid support, a capture reagent, and a signal generating material. The kit can also include instructions for using the devices and reagents, handling the sample, and analyzing the data. Further the kit may be used with a computer system or software to analyze and report the result of the analysis of the biological sample.

The kits can also contain one or more reagents (e.g., solubilization buffers, detergents, washes, or buffers) for processing a biological sample. Any of the kits described herein can also include, e.g., buffers, blocking agents, mass spectrometry matrix materials, antibody capture agents, positive control samples, negative control samples, software and information such as protocols, guidance and reference data.

In some embodiments, kits are provided for the analysis of NAFLD and/or NASH, wherein the kits comprise PCR primers for one or more biomarkers described herein. In some embodiments, a kit may further include instructions for use and correlation of the biomarkers with NAFLD and/or NASH prognosis. In some embodiments, a kit may include a DNA array containing the complement of one or more of the biomarkers described herein, reagents, and/or enzymes for amplifying or isolating sample DNA. The kits may include reagents for real-time PCR, for example, TaqMan probes and/or primers, and enzymes.

For example, a kit can comprise (a) reagents comprising at least one capture reagent for determining the level of one or more biomarkers in a test sample, and optionally (b) one or more algorithms or computer programs for performing the steps of comparing the amount of each biomarker quantified in the test sample to one or more predetermined cutoffs. In some embodiments, an algorithm or computer program assigns a score for each biomarker quantified based on said comparison and, in some embodiments, combines the assigned scores for each biomarker quantified to obtain a total score. Further, in some embodiments, an algorithm or computer program compares the total score with a predetermined score, and uses the comparison to determine whether the individual has NAFLD, steatosis and/or NASH. Alternatively, rather than one or more algorithms or computer programs, one or more instructions for manually performing the above steps by a human can be provided.

Computer Methods and Software

Once a biomarker or biomarker panel is selected, a method for assessing NAFLD in an individual may comprise the following: 1) collect or otherwise obtain a biological sample; 2) perform an analytical method to detect and measure the biomarker or biomarkers in the panel in the biological sample; and 3) report the results of the biomarker levels. In some embodiments, the results of the biomarker levels are reported qualitatively rather than quantitatively, such as, for example, a proposed diagnosis ("NAFLD," "steatosis," "NASH," "NASH stage 2, 3 or 4," etc.) or simply a positive/negative result where "positive" and "negative" are defined. In some embodiments, a method for assessing NAFLD in an individual may comprise the following: 1) collect or otherwise obtain a biological sample; 2) perform an analytical method to detect and measure the biomarker or biomarkers in the panel in the biological sample; 3) perform any data normalization or standardization; 4) calculate each biomarker level; and 5) report the results of the biomarker levels. In some embodiments, the biomarker levels are combined in some way and a single value for the combined biomarker levels is reported. In this approach, in some embodiments, the reported value may be a single number determined from the sum of all the biomarker calculations that is compared to a pre-set threshold value that is an indication of the presence or absence of disease. Or the diagnostic score may be a series of bars that each represent a biomarker value and the pattern of the responses may be compared to a pre-set pattern for determination of the presence or absence of disease.

Figure 9:
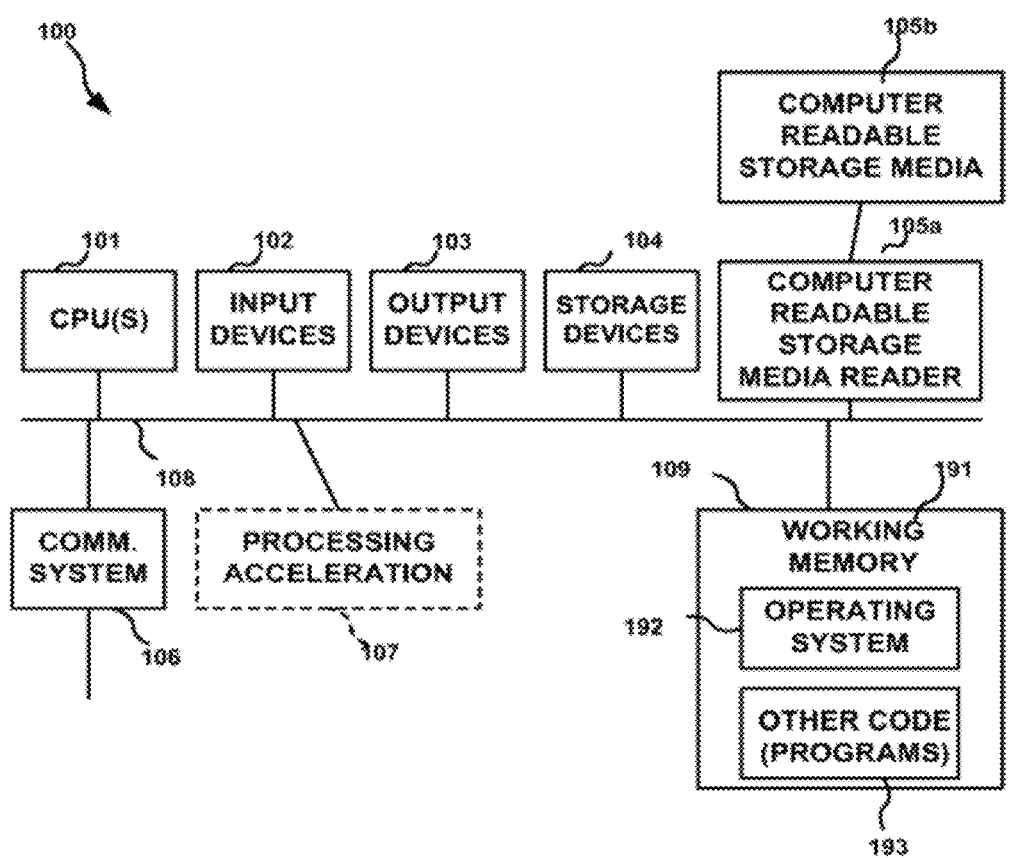
FIG. 9 illustrates a nonlimiting exemplary computer system for use with various computer-implemented methods described herein.
Figure 10:
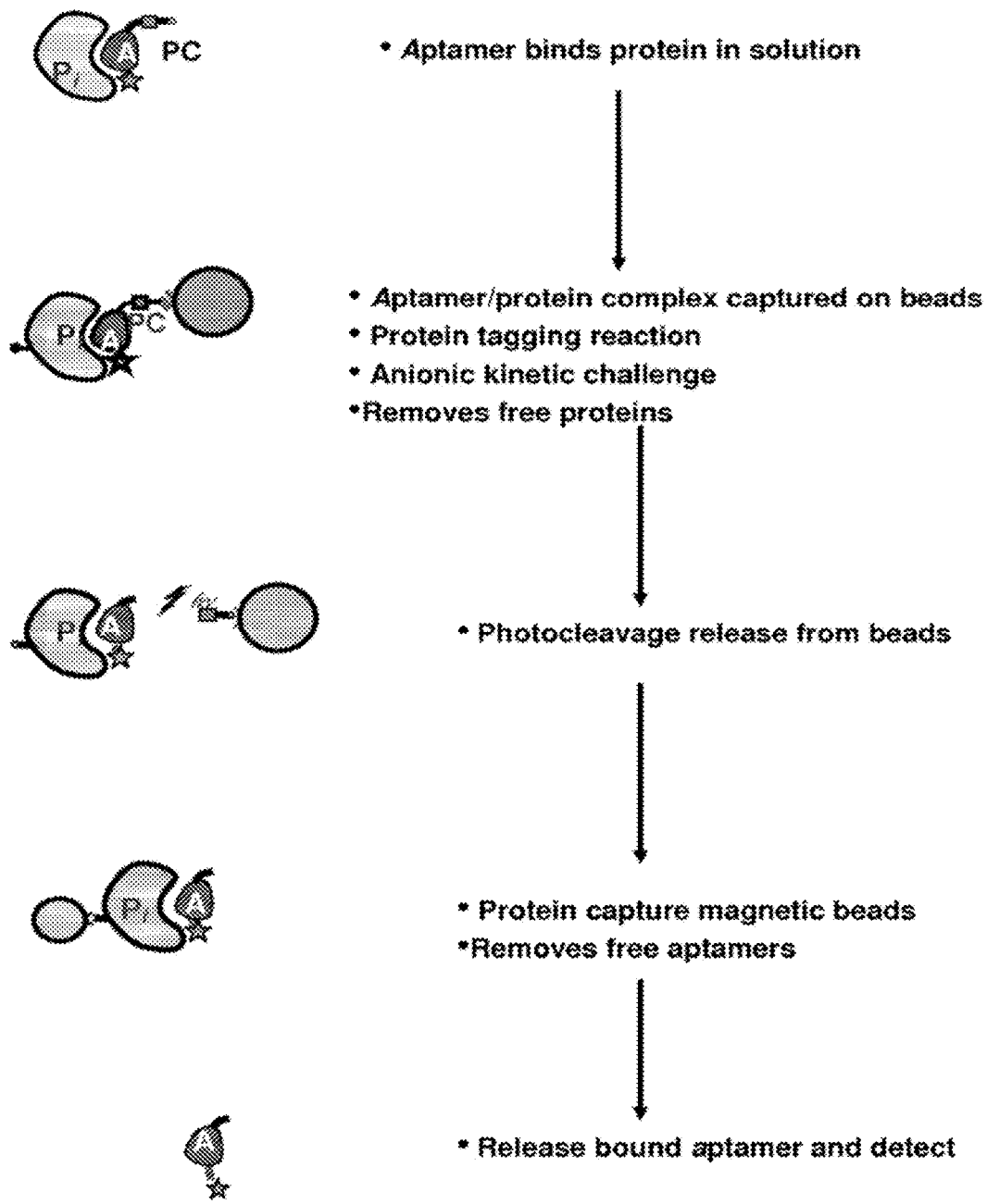
FIG. 10 illustrates a nonlimiting exemplary aptamer assay that can be used to detect one or more biomarkers in a biological sample.

At least some embodiments of the methods described herein can be implemented with the use of a computer. An example of a computer system 100 is shown in FIG. 9. With reference to FIG. 9, system 100 is shown comprised of hardware elements that are electrically coupled via bus 108, including a processor 101, input device 102, output device 103, storage device 104, computer-readable storage media reader 105a, communications system 106 processing acceleration (e.g., DSP or special-purpose processors) 107 and memory 109. Computer-readable storage media reader 105a is further coupled to computer-readable storage media 105b, the combination comprehensively representing remote, local, fixed and/or removable storage devices plus storage media, memory, etc. for temporarily and/or more permanently containing computer-readable information, which can include storage device 104, memory 109 and/or any other such accessible system 100 resource. System 100 also comprises software elements (shown as being currently located within working memory 191) including an operating system 192 and other code 193, such as programs, data and the like.

With respect to FIG. 9, system 100 has extensive flexibility and configurability. Thus, for example, a single architecture might be utilized to implement one or more servers that can be further configured in accordance with currently desirable protocols, protocol variations, extensions, etc. However, it will be apparent to those skilled in the art that embodiments may well be utilized in accordance with more specific application requirements. For example, one or more system elements might be implemented as sub-elements within a system 100 component (e.g., within communications system 106). Customized hardware might also be utilized and/or particular elements might be implemented in hardware, software or both. Further, while connection to other computing devices such as network input/output devices (not shown) may be employed, it is to be understood that wired, wireless, modem, and/or other connection or connections to other computing devices might also be utilized.

In one aspect, the system can comprise a database containing features of biomarkers characteristic of NAFLD and/or NASH. The biomarker data (or biomarker information) can be utilized as an input to the computer for use as part of a computer implemented method. The biomarker data can include the data as described herein.

In one aspect, the system further comprises one or more devices for providing input data to the one or more processors.

The system further comprises a memory for storing a data set of ranked data elements.

In another aspect, the device for providing input data comprises a detector for detecting the characteristic of the data element, e.g., such as a mass spectrometer or gene chip reader.

The system additionally may comprise a database management system. User requests or queries can be formatted in an appropriate language understood by the database management system that processes the query to extract the relevant information from the database of training sets.

The system may be connectable to a network to which a network server and one or more clients are connected. The network may be a local area network (LAN) or a wide area network (WAN), as is known in the art. Preferably, the server includes the hardware necessary for running computer program products (e.g., software) to access database data for processing user requests.

The system may include an operating system (e.g., UNIX® or Linux) for executing instructions from a database management system. In one aspect, the operating system can operate on a global communications network, such as the internet, and utilize a global communications network server to connect to such a network.

The system may include one or more devices that comprise a graphical display interface comprising interface elements such as buttons, pull down menus, scroll bars, fields for entering text, and the like as are routinely found in graphical user interfaces known in the art. Requests entered on a user interface can be transmitted to an application program in the system for formatting to search for relevant information in one or more of the system databases. Requests or queries entered by a user may be constructed in any suitable database language.

The graphical user interface may be generated by a graphical user interface code as part of the operating system and can be used to input data and/or to display inputted data. The result of processed data can be displayed in the interface, printed on a printer in communication with the system, saved in a memory device, and/or transmitted over the network or can be provided in the form of the computer readable medium.

The system can be in communication with an input device for providing data regarding data elements to the system (e.g., expression values). In one aspect, the input device can include a gene expression profiling system including, e.g., a mass spectrometer, gene chip or array reader, and the like.

The methods and apparatus for analyzing biomarker information according to various embodiments may be implemented in any suitable manner, for example, using a computer program operating on a computer system. A conventional computer system comprising a processor and a random access memory, such as a remotely-accessible application server, network server, personal computer or workstation may be used. Additional computer system components may include memory devices or information storage systems, such as a mass storage system and a user interface, for example a conventional monitor, keyboard and tracking device. The computer system may be a stand-alone system or part of a network of computers including a server and one or more databases.

The biomarker analysis system can provide functions and operations to complete data analysis, such as data gathering, processing, analysis, reporting and/or diagnosis. For example, in one embodiment, the computer system can execute the computer program that may receive, store, search, analyze, and report information relating to the biomarkers. The computer program may comprise multiple modules performing various functions or operations, such as a processing module for processing raw data and generating supplemental data and an analysis module for analyzing raw data and supplemental data to generate a disease status and/or diagnosis. Identifying NAFLD, steatosis, and/or NASH may comprise generating or collecting any other information, including additional biomedical information, regarding the condition of the individual relative to the disease, identifying whether further tests may be desirable, or otherwise evaluating the health status of the individual.

Some embodiments described herein can be implemented so as to include a computer program product. A computer program product may include a computer readable medium having computer readable program code embodied in the medium for causing an application program to execute on a computer with a database.

As used herein, a "computer program product" refers to an organized set of instructions in the form of natural or programming language statements that are contained on a physical media of any nature (e.g., written, electronic, magnetic, optical or otherwise) and that may be used with a computer or other automated data processing system. Such programming language statements, when executed by a computer or data processing system, cause the computer or data processing system to act in accordance with the particular content of the statements. Computer program products include without limitation: programs in source and object code and/or test or data libraries embedded in a computer readable medium. Furthermore, the computer program product that enables a computer system or data processing equipment device to act in pre-selected ways may be provided in a number of forms, including, but not limited to, original source code, assembly code, object code, machine language, encrypted or compressed versions of the foregoing and any and all equivalents.

In one aspect, a computer program product is provided for indicating whether an individual has NAFLD, whether an individual has steatosis, and/or whether an individual has NASH (such as stage 1, 2, 3, or 4 NASH, or stage 2, 3, or 4 NASH). The computer program product includes a computer readable medium embodying program code executable by a processor of a computing device or system, the program code comprising: code that retrieves data attributed to a biological sample from an individual, wherein the data comprises biomarker levels that correspond to one or more of the biomarkers described herein, and code that executes a classification method that indicates the NAFLD, steatosis, and/or NASH status of the individual as a function of the biomarker levels.

While various embodiments have been described as methods or apparatuses, it should be understood that embodiments can be implemented through code coupled with a computer, e.g., code resident on a computer or accessible by the computer. For example, software and databases could be utilized to implement many of the methods discussed above. Thus, in addition to embodiments accomplished by hardware, it is also noted that these embodiments can be accomplished through the use of an article of manufacture comprised of a computer usable medium having a computer readable program code embodied therein, which causes the enablement of the functions disclosed in this description. Therefore, it is desired that embodiments also be considered protected by this patent in their program code means as well. Furthermore, the embodiments may be embodied as code stored in a computer-readable memory of virtually any kind including, without limitation, RAM, ROM, magnetic media, optical media, or magneto-optical media. Even more generally, the embodiments could be implemented in software, or in hardware, or any combination thereof including, but not limited to, software running on a general purpose processor, microcode, programmable logic arrays (PLAs), or application-specific integrated circuits (ASICs).

It is also envisioned that embodiments could be accomplished as computer signals embodied in a carrier wave, as well as signals (e.g., electrical and optical) propagated through a transmission medium. Thus, the various types of information discussed above could be formatted in a structure, such as a data structure, and transmitted as an electrical signal through a transmission medium or stored on a computer readable medium.

Methods of Treatment

In some embodiments, following a determination that a subject has NAFLD, steatosis, or NASH, the subject undergoes a therapeutic regimen to delay or prevent worsening of the disease. Nonlimiting exemplary therapeutic regimens for NAFLD, steatosis, and/or NASH include weight loss, blood sugar control, and alcohol avoidance. In some embodiments, a subject is given a therapeutic agent, such as pioglitazone, vitamin E, and/or metformin. See, e.g., Sanyal et al., 2010, *NEJM*, 362: 1675-1685. In some embodiments, a subject undergoes gastric bypass (or similar) surgery, for example, in order to accelerate weight loss.

In some embodiments, methods of monitoring NAFLD are provided. In some embodiments, the present methods of determining whether a subject has NAFLD are carried out at a time 0. In some embodiments, the method is carried out again at a time 1, and optionally, a time 2, and optionally, a time 3, etc., in order to monitor the progression of the NAFLD in the subject. In some embodiments, different biomarkers are used at different time points, depending on the current state of the individual's disease and/or depending on the rate at which the disease is believed or predicted to progress.

Other Methods

In some embodiments, the biomarkers and methods described herein are used to determine a medical insurance premium and/or a life insurance premium. In some embodiments, the results of the methods described herein are used to determine a medical insurance premium and/or a life insurance premium. In some such instances, an organization that provides medical insurance or life insurance requests or otherwise obtains information concerning a subject's NAFLD or NASH status and uses that information to determine an appropriate medical insurance or life insurance premium for the subject. In some embodiments, the test is requested by, and paid for by, the organization that provides medical insurance or life insurance.

In some embodiments, the biomarkers and methods described herein are used to predict and/or manage the utilization of medical resources. In some such embodiments, the methods are not carried out for the purpose of such prediction, but the information obtained from the method is used in such a prediction and/or management of the utilization of medical resources. For example, a testing facility or hospital may assemble information from the present methods for many subjects in order to predict and/or manage the utilization of medical resources at a particular facility or in a particular geographic area.

EXAMPLES

The following examples are provided for illustrative purposes only and are not intended to limit the scope of the application as defined by the appended claims. Routine molecular biology techniques described in the following examples can be carried out as described in standard laboratory manuals, such as Sambrook et al., Molecular Cloning: A Laboratory Manual, 3rd. ed., Cold Spring Harbor Laboratory Press, Cold Spring Harbor, N.Y., (2001).

Example 1

NAFLD Study Subjects

The samples used for identifying biomarkers were from Geisinger Health. Serum samples were collected and liver biopsies were performed on 443 obese patients before they underwent bariatric surgery for weight loss.

Samples were collected in red top serum tubes and processed per protocol; briefly, a sample was allowed to clot for 30 minutes at room temperature, and then centrifuged at 1300×g for 10 minutes and the top layer was removed and stored at −80° C. Samples were thawed once for aliquoting and once for the assay.

In order to identify biomarkers that will distinguish subjects with NAFLD from normal obese subjects, and biomarkers that will distinguish subjects with NASH from subjects with steatosis in the liver, the study subjects were divided into normal, three levels of liver steatosis (mild, moderate, and severe steatosis), and four stages of NASH according to the liver biopsy results, using the Brunt classification method (Brunt et al., 2007, *Modern Pathol.*, 20: S40-S48). The groups were subclassified as shown in Table 1.

TABLE 1

Subclassification of steatosis and NASH stage groups

| Group | Steato-sis | Inflam-mation | Balloon-ing | Fibro-sis |
|---|---|---|---|---|
| Obese controls | 0 | 0 | 0 | 0 |
| Mild steatosis | 1 | 0 or 1 | 0 | 0 |
| Moderate steatosis | 2 | 0, 1 or 2 | 0 | 0 |
| Severe steatosis | 3 | 0 or 2 | 0 | 0 |
| NASH stage 1 | 1, 2 or 3 | 0 or 1 | 1 | 1 |
| NASH stage 2 | 1, 2 or 3 | 0, 1 or 2 | 2 | 2 |
| NASH stage 3 (bridging) | 1, 2 or 3 | 0, 1 or 2 | 2 | 3 |
| NASH stage 4 (cirrhosis) | 1, 2 or 3 | 0, 1 or 2 | 2 | 4 |

Subject Demographics

Certain characteristics for the individuals in each of the groups discussed above are shown in Table 2.

TABLE 2

Subject demographics

| Group | # Female | # Male | Total | # Blinded | Age at biopsy, mean years | BMI, mean kg/m$^2$ | LDL, mean mg/dl | % with Diabetes |
|---|---|---|---|---|---|---|---|---|
| Control | 111 | 14 | 125 | 37 | 44.59 | 46.8 | 107.86 | 28 (22.4%) |
| Mild Steatosis | 44 | 7 | 51 | 10 | 45.75 | 46.6 | 112.12 | 15 (29.4%) |
| Moderate Steatosis | 25 | 7 | 32 | 10 | 44.5 | 44.77 | 103.29 | 12 (37.5%) |
| Severe Steatosis | 45 | 9 | 54 | 17 | 47.11 | 47.75 | 101.11 | 23 (42.6%) |
| NASH Stage 1 | 93 | 20 | 113 | 37 | 46.69 | 47.29 | 103.37 | 58(51.3%) |
| NASH Stage 2 | 27 | 11 | 38 | 12 | 48.52 | 48.9 | 109.74 | 22 (57.9%) |
| NASH Stage 3 | 12 | 8 | 20 | 0 | 50.05 | 46.27 | 101.06 | 17(85%) |
| NASH Stage 4 | 6 | 4 | 10 | 0 | 48.7 | 47.22 | 101.9 | 5 (50%) |
| Total | 363 | 80 | 443 | | | | | |

As shown in Table 1, age, body mass index, and LDL levels were determined for the subjects, and found to be balanced across all groups.

Example 2

Multiplex Aptamer Assay for Biomarker Identification

The sample quality of the normal, NAFLD, and NASH samples in the groups mentioned above were assessed by comparing distributions of biomarkers associated with sample handling, such as shear, cell lysis, and complement activation in the cases and controls. The sample quality was good, and there was no case control bias.

A multiplex aptamer assay was used to analyze the samples and controls to identify biomarkers predictive of NAFLD and NASH. The multiplexed analysis used in this experiment included aptamers to detect 1129 proteins in blood from small sample volumes (~65 μl of serum or plasma), with low limits of detection (1 pM median), ~7 logs of dynamic range, and ~5% median coefficient of variation. The multiplex aptamer assay is described, e.g., in Gold et al. (2010) Aptamer-Based Multiplexed Proteomic Technology for Biomarker Discovery. PLoS ONE 5(12): e15004; and U.S. Publication Nos: 2012/0101002 and 2012/0077695.

Stability Selection takes many subsets of half the data and performs biomarker selection using the lasso classifier, which is a regularized logistic regression model. See, e.g., Meinshausen et al., 2010, *J. Royal Statistical Soc: Series B (Statistical Methodology)*, 72: 417-473. The selection path for a single biomarker is the proportion of these subsets for which that biomarker was selected by the lasso model over a range of lambda. Lambda is a tuning parameter which determines how many biomarkers are selected by the lasso. The maximum selection probability over a range of lambda values is the ultimate metric used to select a set of biomarkers.

Candidate biomarkers were identified by stability selection, which were then used to generate the random forest classifier model. See, e.g., Shi et al., *J. Comput. Graph. Stat.* 15(1): 118-138 (2006). Briefly, a random forest predictor is an ensemble of individual classification tree predictors. See, e.g., Breiman, *Machine Learning*, 45(1): 5-32 (2001). For each observation, each individual tree votes for one class and the forest predicts the class that has the plurality of votes. The user specifies the number of randomly selected variables (mtry) to be searched through for the best split at each node. The Gini index is used as the splitting criterion. See, e.g., Breiman et al., Classification and Regression Trees, Chapman and Hall, New York, 1984. The largest tree possible is grown and is not pruned. The root node of each tree in the forest contains a bootstrap sample from the original data as the training set. The observations that are not in the training set, roughly 1/3 of the original data set, are referred to as out-of-bag (OOB) observations. One can arrive at OOB predictions as follows: for a case in the original data, predict the outcome by plurality vote involving only those trees that did not contain the case in their corresponding bootstrap sample. By contrasting these OOB predictions with the training set outcomes, one can arrive at an estimate of the prediction error rate, which is referred to as the OOB error rate.

Univariate analysis was performed using the non-parametric Kolmogorov-Smirnov test (KS statistics), which quantifies the distance between the cumulative distribution function of each aptamer for two reference distributions designated case (mild, moderate and severe steatosis and/or NASH 1-4) and control (normal obese). The performance of the random forest classifier is dependent upon the number and quality of the biomarkers used to construct and train the classifier. A single biomarker will perform in accordance with its KS-distance and its PCA (principal component analysis) value as exemplified herein. If a classifier performance metric is defined as the sum of the sensitivity (fraction of true positives, $f_{TP}$) and specificity (one minus the fraction of false positives, $1-f_{FP}$), a perfect classifier will have a score of two and a random classifier, on average, will have a score of one. Using the definition of the KS-distance, that value x* which maximizes the difference in the cdf (cumulative distribution function) functions can be found by solving $$\frac{\partial KS}{\partial x} = \frac{\partial (cdf_c(x) - cdf_d(x))}{\partial x} = 0$$

for x which leads to p(x*|c)=p(x*|d), i.e., the KS distance occurs where the class-dependent pdfs (probability density functions) cross. Substituting this value of x* into the expression for the KS-distance yields the following definition for KS $$KS = cdf_c(x^*) - cdf_d(x^*)$$

$$= \int_{-\infty}^{x^*} p(x \mid c) dx - \int_{-\infty}^{x^*} p(x \mid d) dx$$

$$= 1 - \int_{x^*}^{\infty} p(x \mid c) dx - \int_{-\infty}^{x^*} p(x \mid d) dx$$

the KS distance is one minus the total fraction of errors using a test with a cut-off at x*, essentially a single analyte Bayesian classifier. Since we define a score of sensitivity+specificity=$2-f_{FP}-f_{FN}$, combining the above definition of the KS-distance we see that sensitivity+specificity=1+KS. We select biomarkers with a statistic that is inherently suited for building classifiers.

The addition of subsequent biomarkers with good KS distances (>0.3, for example) will, in general, improve the classification performance if the subsequently added biomarkers are independent of the first biomarker. Using the sensitivity plus specificity as a classifier score, many high scoring classifiers may be generated.

A. Steatosis Classifier

Based on the subject classifications, we assumed that all steatosis groups as well as NASH stages 1-4 have fat in the liver cells. A classifier (steatosis, or fat in the liver) was developed by comparing obese normal subjects to all NAFLD subjects.

Markers chosen by stability selection (see FIG. 1) were supplied to a random forest algorithm to generate a model. The resulting ROC curve is provided (see below).

Figure 2:
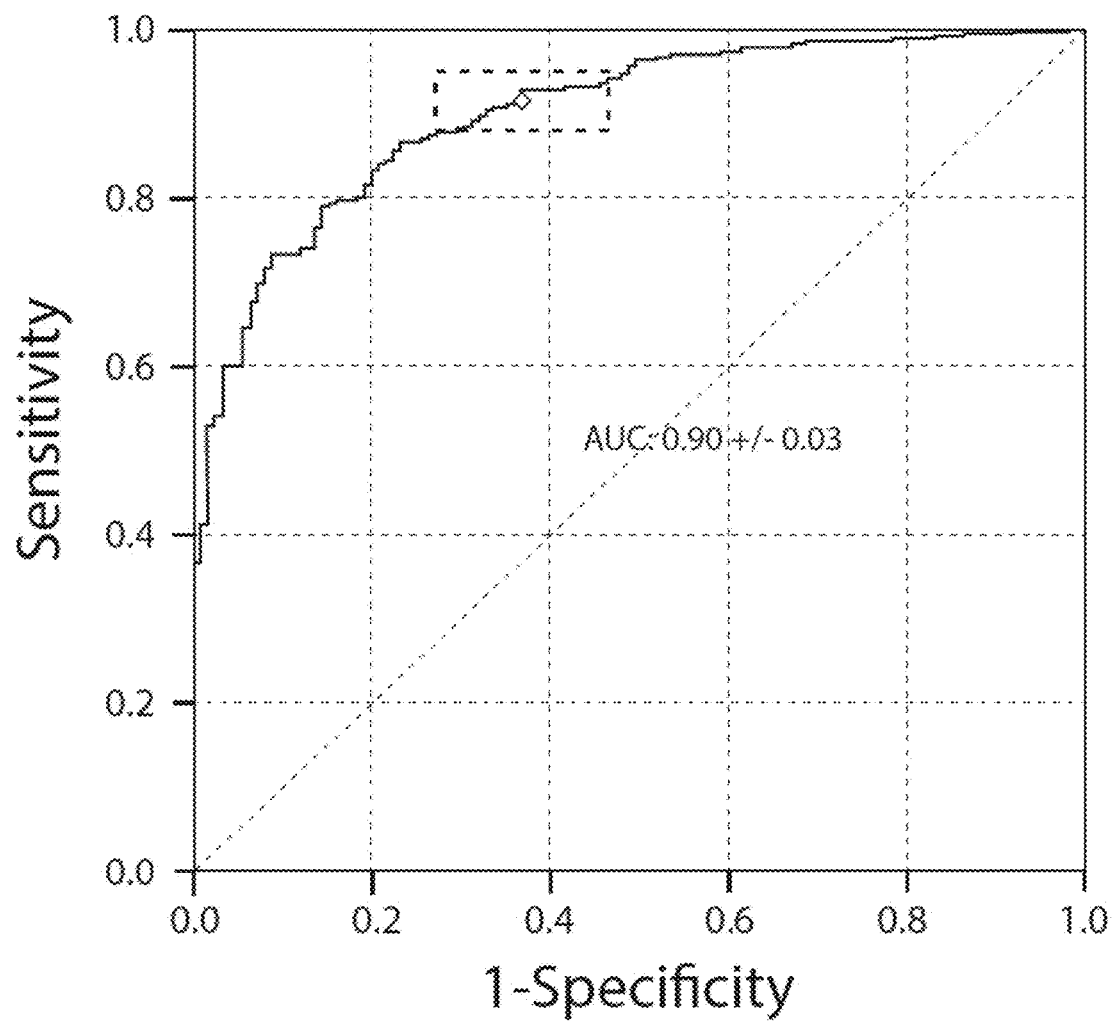
FIG. 2 shows a ROC curve of a nine biomarker classifier for steatosis, as described in Example 2.

A ROC curve for a nine marker classifier for NAFLD (steatosis) is shown in FIG. 2. The area under the curve (AUC) was 0.90+/−0.03. The sensitivity was 92% and the specificity was 63%, with a cutoff of 0.5.

Figure 3:
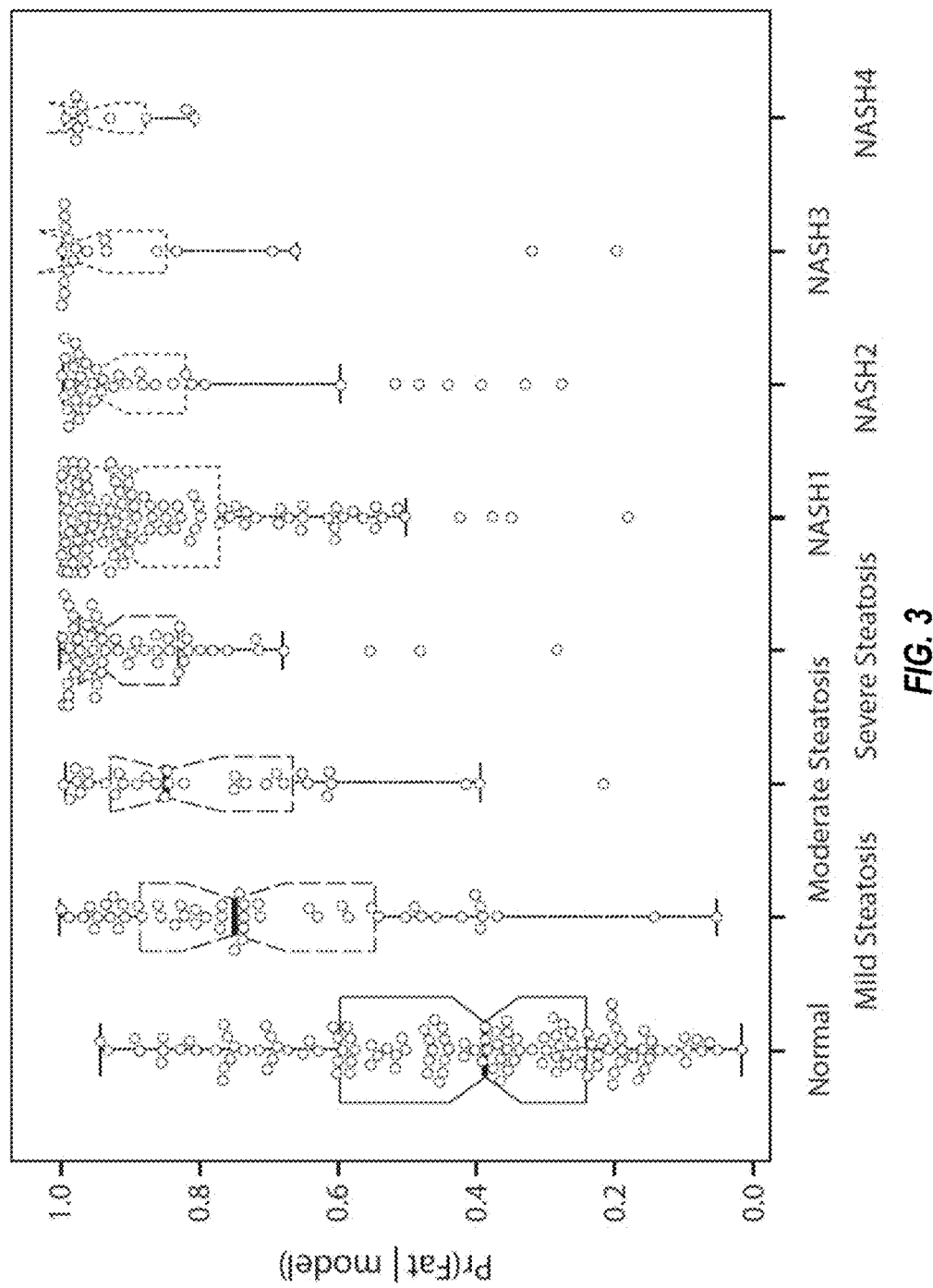
FIG. 3 shows the vote by class for the nine-marker random forest classifier for steatosis, as described in Example 2.

The probability score, i.e. Prob(Steatosis), from the model of each classifier was plotted for each individual across all groups to assess whether it could be used as a severity/monitoring model in addition to the binary decision on which it was constructed (FIG. 3). The plot shows a clear discrimination between no steatosis and steatosis and probability vote increases with the level of steatosis. NASH subjects at all stages have severe steatosis.

Figure 4:
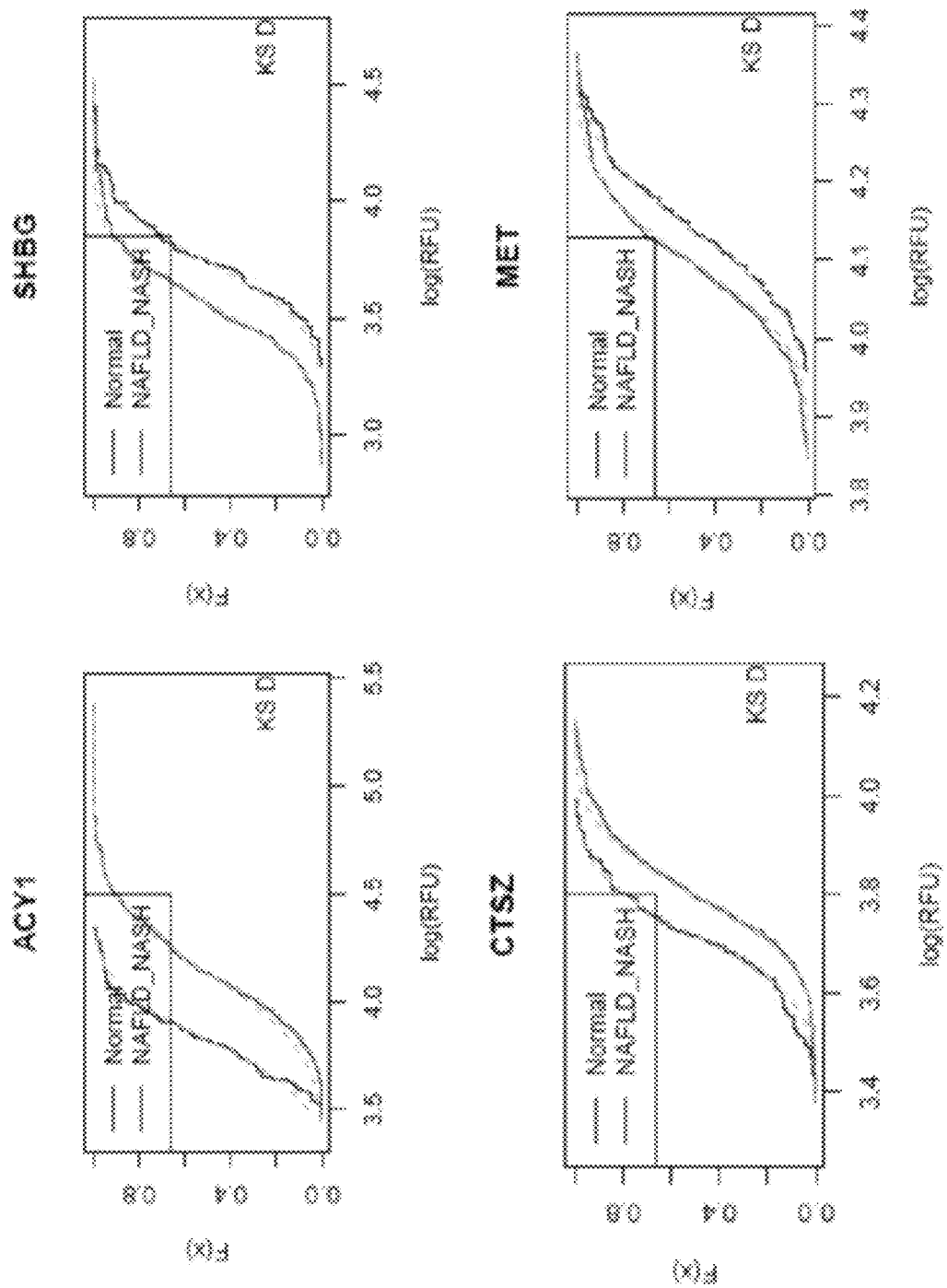
FIG. 4 shows the cumulative distribution functions for each of the biomarkers in the nine-marker classifier for steatosis, as described in Example 2.
Figure 4:
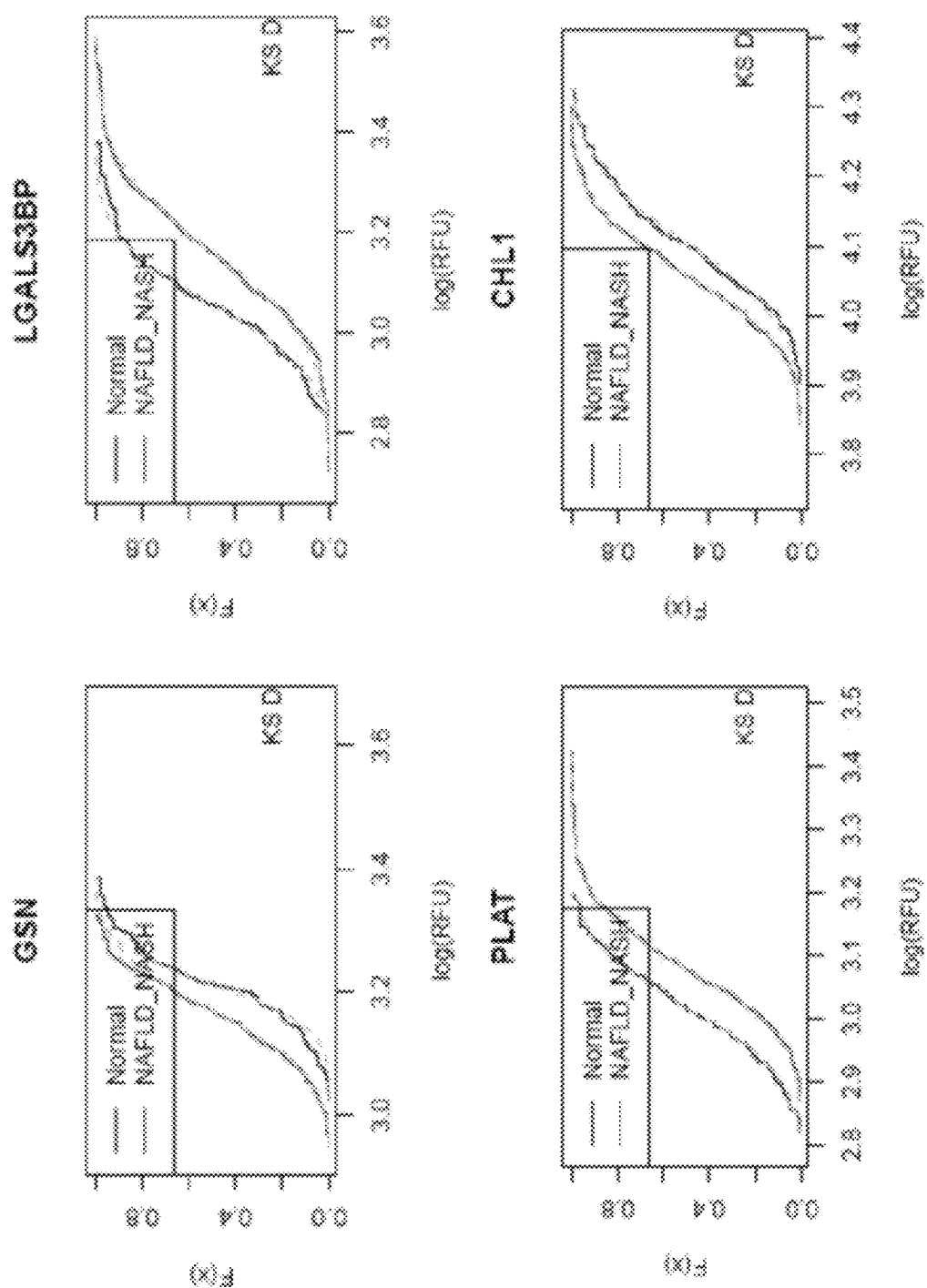
Figure 4:
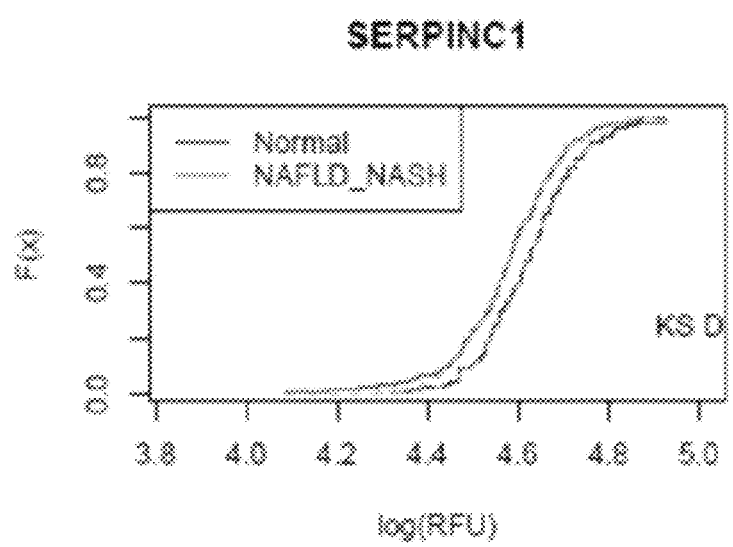

FIG. 4 shows the cumulative distribution functions (CDFs) for the 9 biomarkers in the classifier.

Table 3 shows the biomarkers in the 9-marker classifier. Table 3 also provides an alternate name for certain biomarkers, the gene name, and the UniProt accession number for each biomarker, and whether the biomarker is present at higher or lower levels in the NAFLD population, as compared to the normal population.

TABLE 3

Nine biomarker classifier for NAFLD

| Biomarker/Aliases | Gene Name | UniProt | Biomarker level higher/lower in all NAFLD population |
|---|---|---|---|
| Aminoacylase-1 | ACY1 | Q03154 | Higher |
| Sex hormone-binding globulin | SHBG | P04278 | Lower |
| Cathepsin Z, Cathepsin P, Cathepsin X | CTSZ | Q9UBR2 | Higher |
| c-met, Hepatocyte growth factor receptor, Met proto-oncogene tyrosine kinase | MET | P08581 | Lower |
| Gelsolin | GSN | P06396 | Lower |
| Galectin-3 binding protein, Lectin galactoside-binding soluble 3-binding protein | LGALS3BP | Q08380 | Higher |
| Tissue-type plasminogen activator, tPA | PLAT | P00750 | Higher |
| Neural cell adhesion molecule L1-like protein | CHL1 | O00533 | Lower |
| Antithrombin III | SERPINC1 | P01008 | Lower |

FIG. 3 shows box plots for the nine biomarker classifier in each of the subject groups (from left to right: normal, mild steatosis, moderate steatosis, severe steatosis, NASH1, NASH2, NASH3, NASH4). The black line within each box represents the median (or 50th percentile) of the data points, and the box itself represents the inter-quartile range (IQR), the area encompassing data points from the 25$^{th}$ to 75$^{th}$ percentile. The whiskers extend to cover data points within 1.5×IQR of the top and bottom of the box.

B. NASH (Fibrosis) Classifier

All subjects with NASH have some form of inflammation and ballooning associated with fibrosis. We therefore compared all steatosis groups with NASH stages 2, 3 and 4. To ensure identification of true fibrosis biomarkers, the NASH stage 1 group was excluded.

Figure 5:
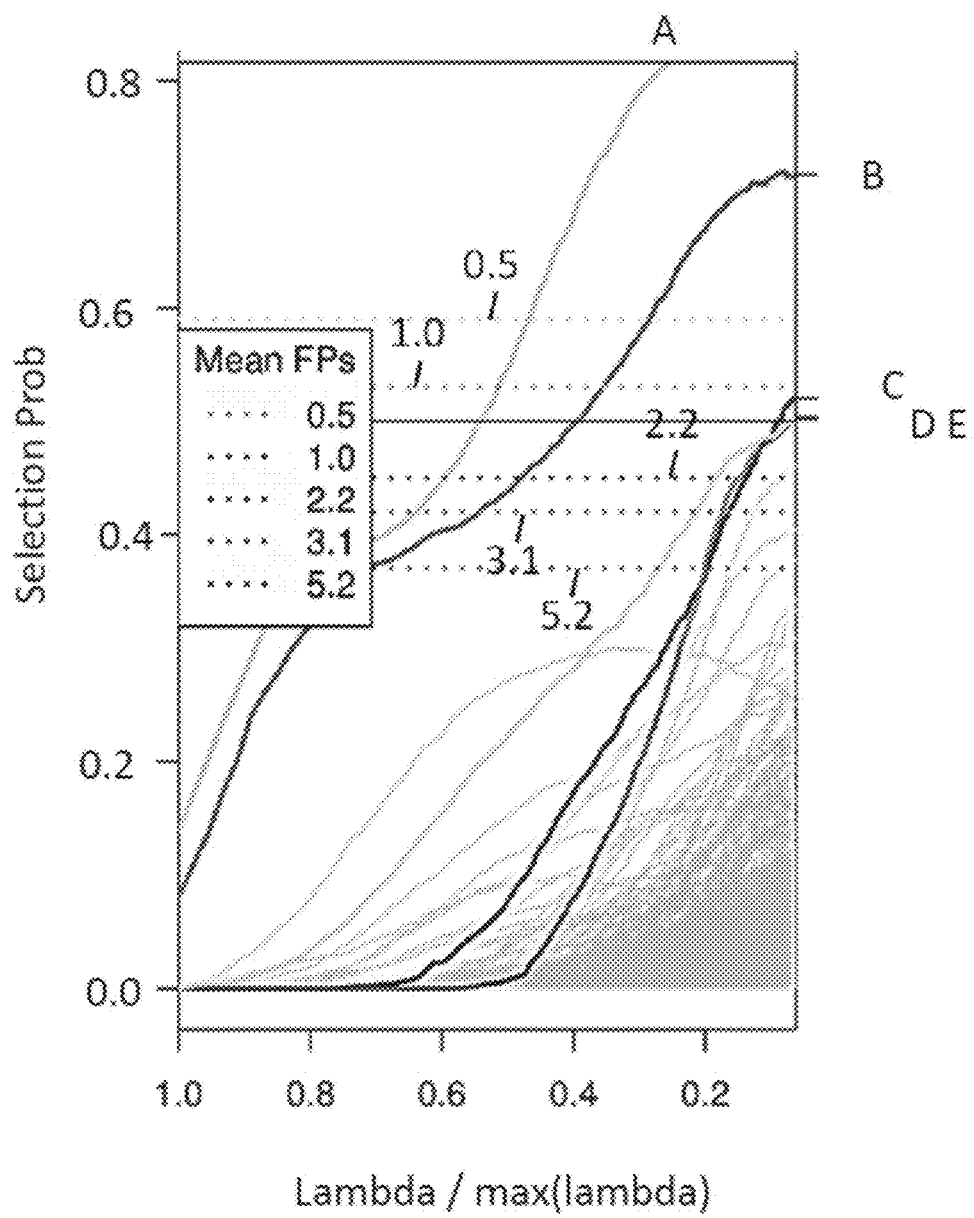
FIG. 5 shows stability selection paths of the NASH (fibrosis) classifier, as described in Example 2.

Markers chosen by stability selection (FIG. 5) were supplied to a random forest algorithm to generate a model. The resulting ROC is provided below.

Figure 6:
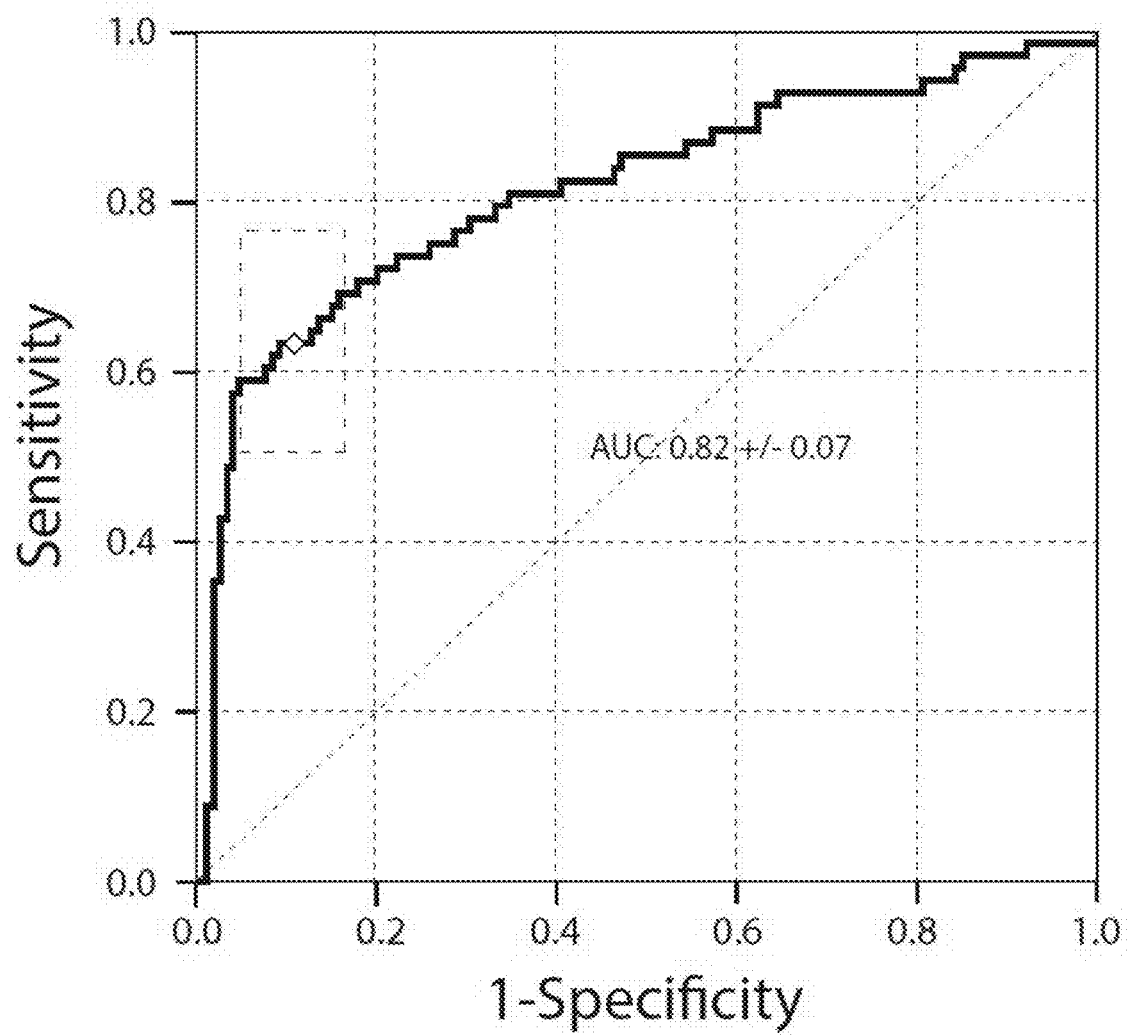
FIG. 6 shows a ROC curve of a four biomarker classifier for NASH (fibrosis), as described in Example 2.

A ROC curve for the four marker classifier for NASH stages 2, 3, and 4 (fibrosis) is shown in FIG. 6. The area under the curve (AUC) was 0.82+/−0.07, with a sensitivity of 62% and a specificity of 92% at a cutoff of 0.5.

Figure 7:
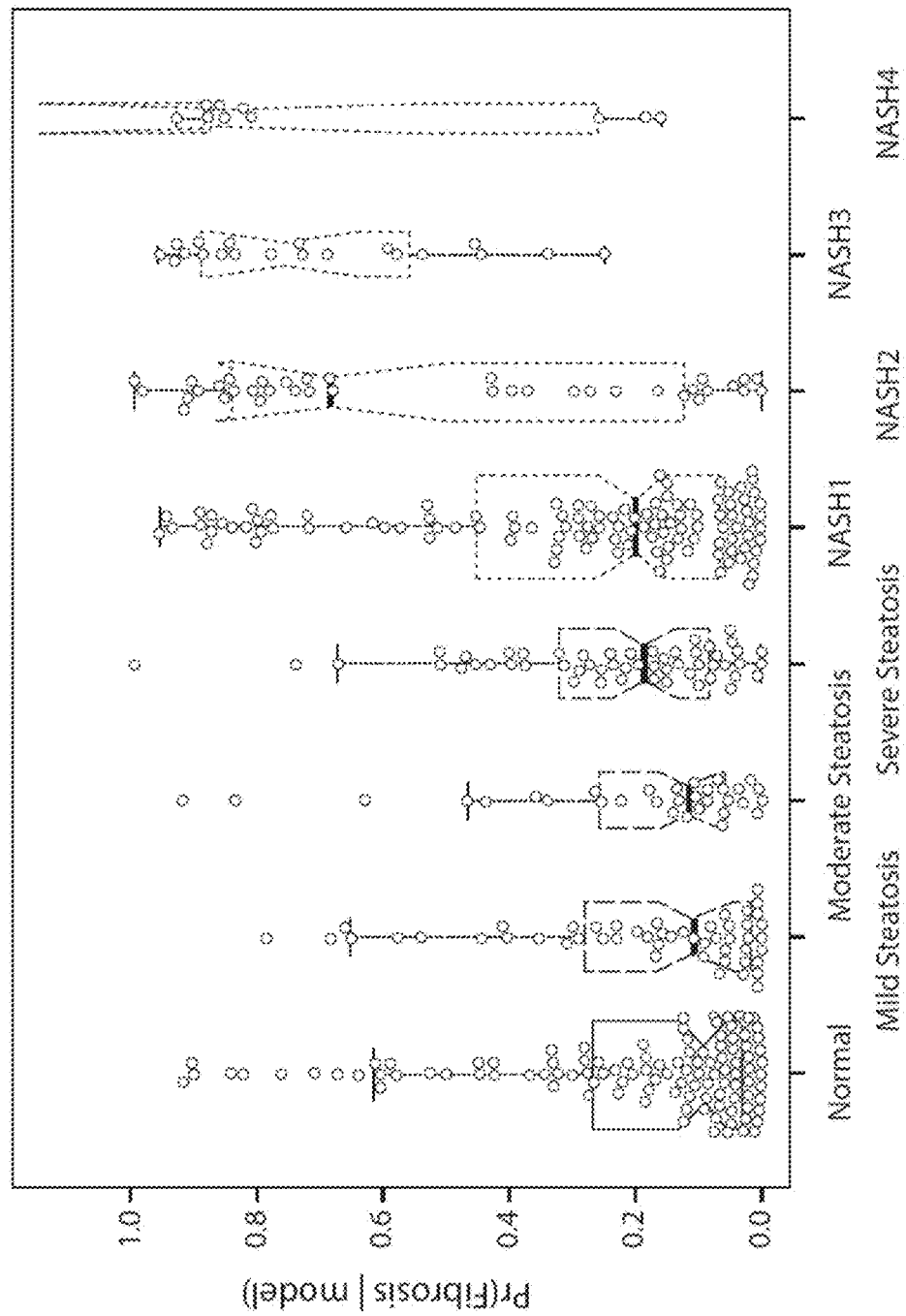
FIG. 7 shows box plots for the four-marker classifier for NASH (fibrosis) in each of the subject groups, as described in Example 2.

The probability score, i.e. Prob(Steatosis), from the model of each classifier was plotted for each individual across all groups to assess whether it could be used as a severity/monitoring model in addition to the binary decision on which it was constructed (FIG. 7). The plot shows a clear discrimination between no steatosis and steatosis and probability vote increases with the level of steatosis. NASH subjects at all stages have severe steatosis.

Table 4 shows the biomarkers in the 4-marker classifier. Table 4 also provides an alternate name for certain biomarkers, the gene name, and the UniProt accession number for each biomarker, and whether the biomarker is present at higher or lower levels in the NASH 2, 3, and 4 populations, as compared to all NAFLD populations.

TABLE 4

Four biomarker classifier for NASH stages 2, 3, and 4 versus steatosis (NAFLD)

| Biomarker/Aliases | Gene Name | UniProt | Biomarker level higher/lower in fibrosis (NASH) population |
|---|---|---|---|
| Complement C7 | C7 | P10643 | Higher |
| Collectin Kidney 1 | COLEC11 | Q9BWP8 | Higher |
| Peptidylprolyl isomerase D | PPID | Q08752 | Higher |
| Insulin-like growth factor-binding protein 3 | IGFBP3 | P17936 | Lower |

FIG. 7 shows box plots for the four biomarker classifier in each of the subject groups (from left to right: normal, mild steatosis, moderate steatosis, severe steatosis, NASH1, NASH2, NASH3, NASH4). The black line within each box represents the median (or $50^{th}$ percentile) of the data points, and the box itself represents the inter-quartile range (IQR), the area encompassing data points from the $25^{th}$ to $75^{th}$ percentile. The whiskers extend to cover data points within 1.5×IQR of the top and bottom of the box.

Figure 8:
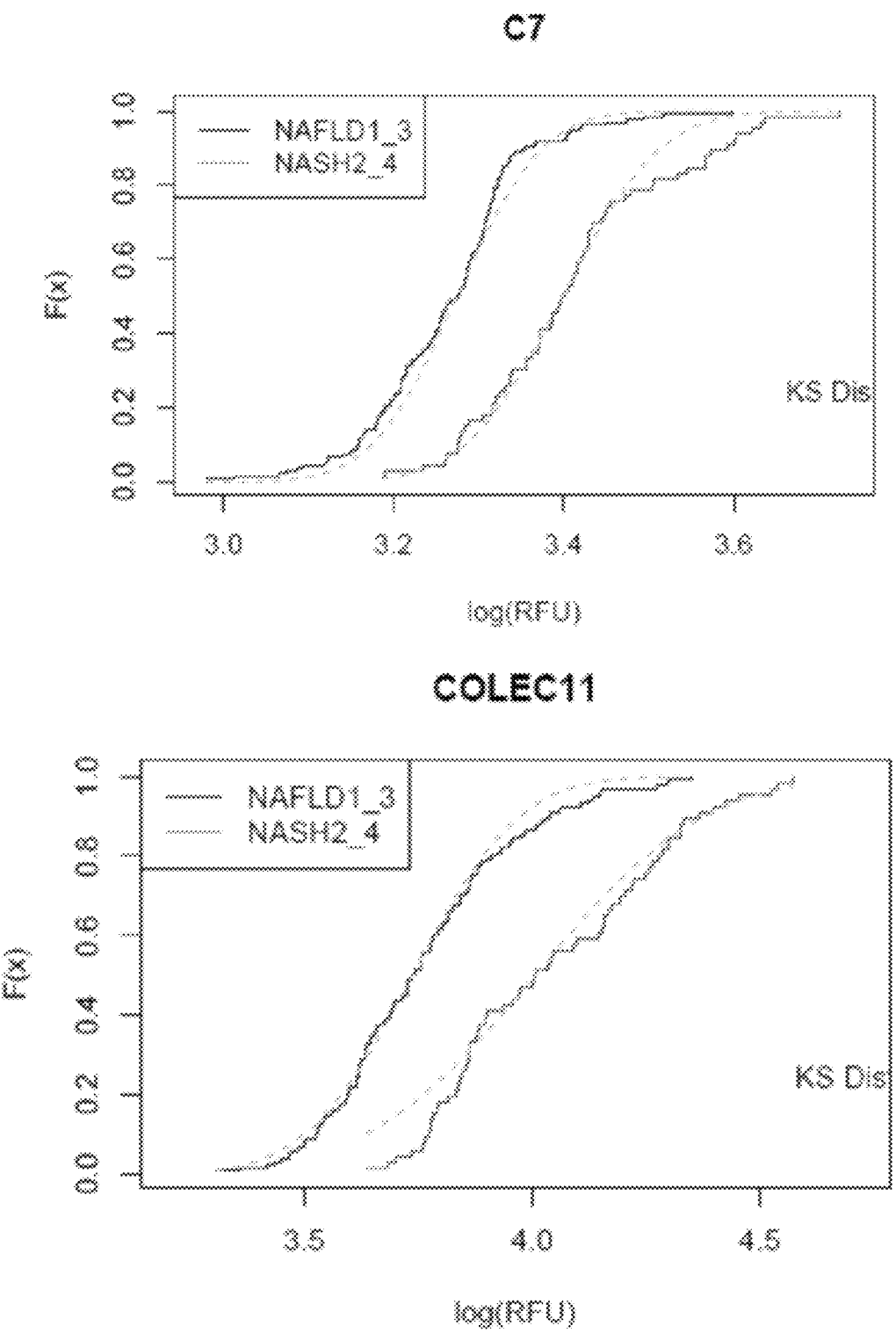
FIG. 8 shows the cumulative distribution functions for each of the biomarkers in the four-marker classifier for NASH (fibrosis), as described in Example 2.
Figure 8:
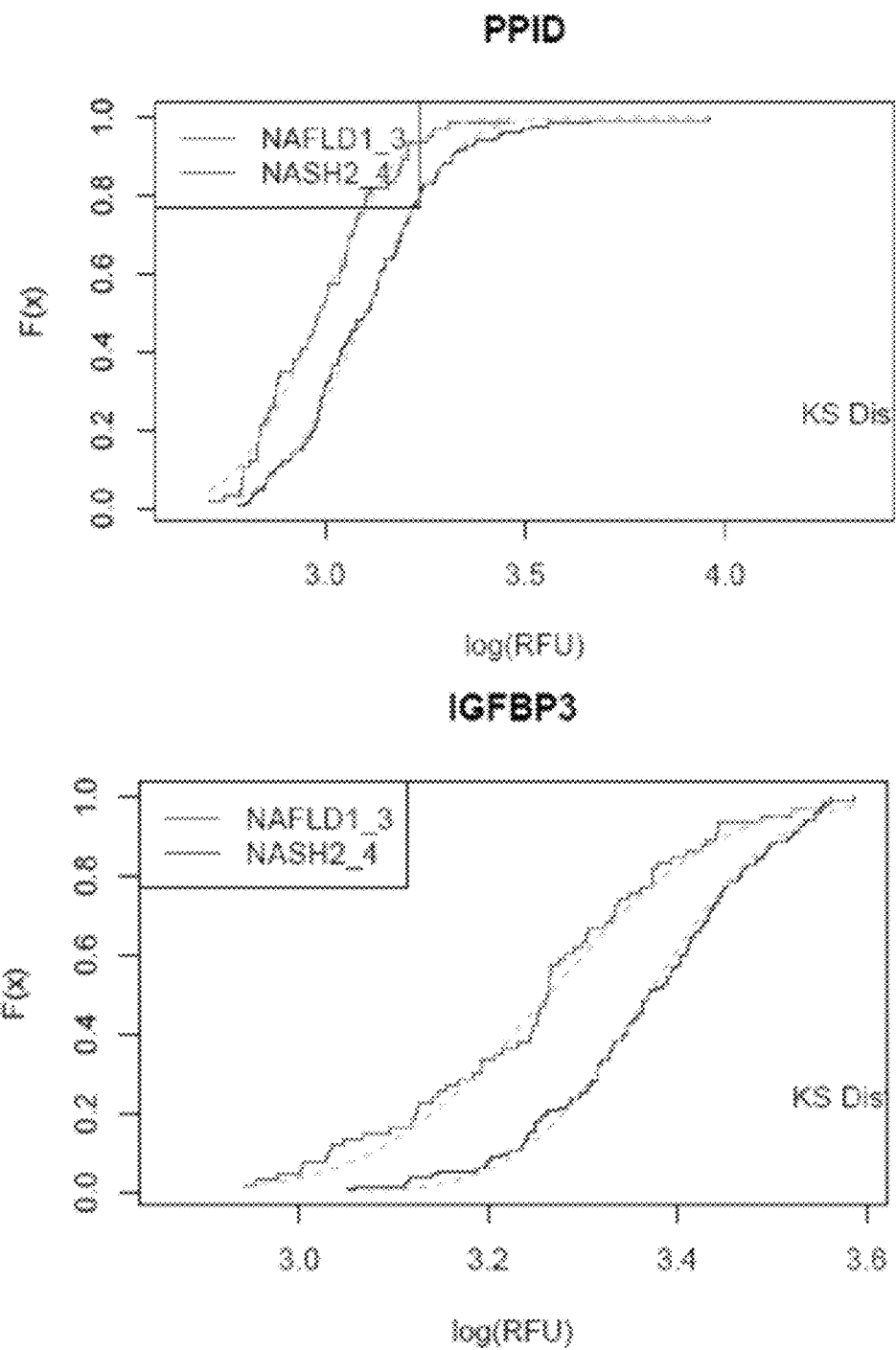

FIG. 8 shows the CDFs for the 4 biomarkers in the classifier.

Example 3

Additional Biomarkers and Classifiers for NAFLD and/or NASH

Stability Selection takes many subsets of half the data and performs biomarker selection using the lasso classifier, which is a regularized logistic regression model. See, e.g., Meinshausen et al., 2010, *J. Royal Statistical Soc: Series B (Statistical Methodology)*, 72: 417-473. The selection path for a single biomarker is the proportion of these subsets for which that biomarker was selected by the lasso model over a range of lambda. Lambda is a tuning parameter which determines how many biomarkers are selected by the lasso. The maximum selection probability over a range of lambda values is the ultimate metric used to select a set of biomarkers.

Using the stability selection method, additional classifiers were defined to distinguish various groups of individuals. The classifiers (including the classifiers discussed above) are shown in Table 5. Markers from comparisons 2 and 5 were used to build a random forest classifier for steatosis (NAFLD) and fibrosis (NASH), as discussed above.

TABLE 5

Classifiers obtained using stability selection

| | Comparison | Sensitivity | Specificity | Markers |
|---|---|---|---|---|
| 1 | Control versus NASH stage 1 to 4 | 0.8641304 | 0.8196721 | ACY, SHBG, LGALS3BP, SIGLEC7, CTSZ, MET, GSN |
| 2 | Control versus (All steatosis + NASH stage 1-4) | 0.8635015 | 0.7452830 | ACY, SHBG, CTSZ, MET, GSN, LGALS3BP, PLAT, CHL1, SERPINC1 |
| 3 | Control versus All steatosis | 0.7664234 | 0.7440000 | ACY, SHBG, SIGLEC14 |
| 4 | All steatosis versus NASH 1 | 0.4901961 | 0.5743243 | TOP1, SIGLEC14 |
| 5 | All steatosis versus NASH stage 2-4 | 0.7543860 | 0.8310811 | C7, COLEC11, PPID, IGFBP3 |
| 6 | All steatosis versus NASH stage 1-4 | 0.6734694 | 0.5983607 | SIGLEC14, AIMP1, TOP1, COLEC11, CA6, STX1A |

*All Steatosis: mild, moderate and severe steatosis

Comparison 1 in Table 5 shows a 7-marker classifier that distinguishes control subjects from NASH stages 1 to 4 with 86.4% sensitivity and 82% specificity. Comparison 3 shows a 3-marker classifier that distinguishes control subjects versus all steatosis (mild, moderate, and severe) with 76.6% sensitivity and 74.4% specificity.

Further information on the biomarkers listed in Table 5 that are not in Tables 3 and 4, above, is shown in Table 6.

TABLE 6

Additional biomarkers for NAFLD and/or NASH

| Biomarker/Aliases | Gene Name | UniProt | Biomarker level higher/lower in NASH versus steatosis versus obese controls |
|---|---|---|---|
| Sialic acid-binding Ig-like lectin 7 | SIGLEC 7 | Q9Y286 | Higher |
| Siglec-14 | SIGLEC14 | Q08ET2 | Higher |
| Topoisomerase I | TOP1 | P11387 | Lower |
| Endothelial-Monocyte Activating Polypeptide 2 (EMAP-2) | AIMP1 | Q12904 | Lower |
| Carbonic anhydrase 6 | CA6 | Q16623 | Lower |
| Syntaxin 1A | STX1A | Q9Y286 | Lower |

The top 25 biomarkers by univariate KS distance for the control group versus NASH stages 1 to 4 are shown in Table 7. These biomarkers, and combinations of these biomarkers, can be used to separate control subjects (such as obese subjects) from subjects with NASH and/or to separate control subjects from subjects with steatosis.

TABLE 7

Top 25 biomarkers

| Biomarker | Signed ks distance | UniProt | Biomarker level higher/lower in NASH versus obese controls |
|---|---|---|---|
| ACY1 | 0.61843 | Q03154 | Higher |
| THBS2 | 0.48071 | P35442 | Higher |
| LGALS3BP | 0.44946 | Q08380 | Higher |
| KYNU | 0.44146 | Q16719 | Higher |
| COLEC11 | 0.43708 | Q9BWP8 | Higher |
| CTSZ | 0.42166 | Q9UBR2 | Higher |
| IL19 | 0.41688 | Q9UHD0 | Higher |
| POR | 0.41021 | P16435 | Higher |
| INS | 0.40888 | P01308 | Higher |
| SHBG | -0.39253 | P04278 | Lower |
| GPT | 0.37459 | Q9H3H5 | Higher |
| GNS | 0.37136 | P15586 | Higher |
| RET | 0.37043 | P07949 | Higher |
| AFM | 0.36986 | P43652 | Higher |
| SELE | 0.36239 | P16581 | Higher |
| CD163 | 0.36146 | Q86VB7 | Higher |

TABLE 7-continued

Top 25 biomarkers

| Biomarker | Signed ks distance | UniProt | Biomarker level higher/lower in NASH versus obese controls |
|---|---|---|---|
| ENPP7 | 0.35518 | Q6UWV6 | Higher |
| IGFBP7 | 0.35063 | Q16270 | Higher |
| GSN | −0.34851 | P06396 | Lower |
| SIGLEC7 | 0.34564 | Q9Y286 | Higher |
| LAMA1.LAMB1.LAMC1 | 0.33401 | P25391 P07942 P11047 | Higher |
| IL18R1 | 0.31973 | Q13478 | Higher |
| FN1 | 0.31898 | P02751 | Higher |
| TGFBI | 0.31823 | Q15582 | Higher |
| AKR1A1 | 0.31421 | P14550 | Higher |

Example 4

Exemplary Biomarker Detection Using Aptamers

An exemplary method of detecting one or more biomarkers in a sample is described, e.g., in Kraemer et al., PLoS One 6(10): e26332, and is described below. Three different methods of quantification: microarray-based hybridization, a Luminex bead-based method, and qPCR, are described.

Reagents

HEPES, NaCl, KCl, EDTA, EGTA, $MgCl_2$ and TWEEN-20 may be purchased, e.g., from Fisher Biosciences. Dextran sulfate sodium salt (DxSO4), nominally 8000 molecular weight, may be purchased, e.g., from AIC and is dialyzed against deionized water for at least 20 hours with one exchange. KOD EX DNA polymerase may be purchased, e.g., from VWR. Tetramethylammonium chloride and CAPSO may be purchased, e.g., from Sigma-Aldrich and streptavidin-phycoerythrin (SAPE) may bepurchased, e.g., from Moss Inc. 4-(2-Aminoethyl)-benzenesulfonylfluoride hydrochloride (AEBSF) may be purchased, e.g., from Gold Biotechnology. Streptavidin-coated 96-well plates may be purchased, e.g., from Thermo Scientific (Pierce Streptavidin Coated Plates HBC, clear, 96-well, product number 15500 or 15501). NHS-PEO4-biotin may be purchased, e.g., from Thermo Scientific (EZ-Link NHS-PEO4-Biotin, product number 21329), dissolved in anhydrous DMSO, and may be stored frozen in single-use aliquots. IL-8, MIP-4, Lipocalin-2, RANTES, MMP-7, and MMP-9 may be purchased, e.g., from R&D Systems. Resistin and MCP-1 may be purchased, e.g., from PeproTech, and tPA may be purchased, e.g., from VWR.

Nucleic Acids

Conventional (including amine- and biotin-substituted) oligodeoxynucleotides may be purchased, e.g., from Integrated DNA Technologies (IDT). Z-Block is a single-stranded oligodeoxynucleotide of sequence 5'-(AC-BnBn) 7-AC-3', where Bn indicates a benzyl-substituted deoxyuridine residue. Z-block may be synthesized using conventional phosphoramidite chemistry. Aptamer capture reagents may also be synthesized by conventional phosphoramidite chemistry, and may be purified, for example, on a 21.5×75 mm PRP-3 column, operating at 80° C. on a Waters Autopurification 2767 system (or Waters 600 series semi-automated system), using, for example, a timberline TL-600 or TL-150 heater and a gradient of triethylammonium bicarbonate (TEAB)/ACN to elute product. Detection is performed at 260 nm and fractions are collected across the main peak prior to pooling best fractions.

Buffers

Buffer SB18 is composed of 40 mM HEPES, 101 mM NaCl, 5 mM KCl, 5 mM $MgCl_2$, and 0.05% (v/v) TWEEN 20 adjusted to pH 7.5 with NaOH. Buffer SB17 is SB18 supplemented with 1 mM trisodium EDTA. Buffer PB1 is composed of 10 mM HEPES, 101 mM NaCl, 5 mM KCl, 5 mM $MgCl_2$, 1 mM trisodium EDTA and 0.05% (v/v) TWEEN-20 adjusted to pH 7.5 with NaOH. CAPSO elution buffer consists of 100 mM CAPSO pH 10.0 and 1 M NaCl. Neutralization buffer contains of 500 mM HEPES, 500 mM HCl, and 0.05% (v/v) TWEEN-20. Agilent Hybridization Buffer is a proprietary formulation that is supplied as part of a kit (Oligo aCGH/ChIP-on-chip Hybridization Kit). Agilent Wash Buffer 1 is a proprietary formulation (Oligo aCGH/ChIP-on-chip Wash Buffer 1, Agilent). Agilent Wash Buffer 2 is a proprietary formulation (Oligo aCGH/ChIP-on-chip Wash Buffer 2, Agilent). TMAC hybridization solution consists of 4.5 M tetramethylammonium chloride, 6 mM trisodium EDTA, 75 mM Tris-HCl (pH 8.0), and 0.15% (v/v) Sarkosyl. KOD buffer (10-fold concentrated) consists of 1200 mM Tris-HCl, 15 mM $MgSO_4$, 100 mM KCl, 60 mM $(NH_4)_2SO_4$, 1% v/v TRITON-X 100 and 1 mg/mL BSA.

Sample Preparation

Serum (stored at −80° C. in 100 μL aliquots) is thawed in a 25° C. water bath for 10 minutes, then stored on ice prior to sample dilution. Samples are mixed by gentle vortexing for 8 seconds. A 6% serum sample solution is prepared by dilution into 0.94× SB17 supplemented with 0.6 mM MgCl2, 1 mM trisodium EGTA, 0.8 mM AEBSF, and 2 μM Z-Block. A portion of the 6% serum stock solution is diluted 10-fold in SB17 to create a 0.6% serum stock. 6% and 0.6% stocks are used, in some embodiments, to detect high- and low-abundance analytes, respectively.

Capture Reagent (Aptamer) and Streptavidin Plate Preparation

Aptamers are grouped into 2 mixes according to the relative abundance of their cognate analytes (or biomarkers). Stock concentrations are 4 nM for each aptamer, and the final concentration of each aptamer is 0.5 nM. Aptamer stock mixes are diluted 4-fold in SB17 buffer, heated to 95° C. for 5 min and cooled to 37° C. over a 15 minute period prior to use. This denaturation-renaturation cycle is intended to normalize aptamer conformer distributions and thus ensure reproducible aptamer activity in spite of variable histories. Streptavidin plates are washed twice with 150 μL buffer PB1 prior to use.

Equilibration and Plate Capture

Heat-cooled 2× Aptamer mixes (55 μL) are combined with an equal volume of 6% or 0.6% serum dilutions, producing equilibration mixes containing 3% and 0.3% serum. The plates are sealed with a Silicone Sealing Mat (Axymat Silicone sealing mat, VWR) and incubated for 1.5 h at 37° C. Equilibration mixes are then transferred to the wells of a washed 96-well streptavidin plate and further incubated on an Eppendorf Thermomixer set at 37° C., with shaking at 800 rpm, for two hours.

Manual Assay

Unless otherwise specified, liquid is removed by dumping, followed by two taps onto layered paper towels. Wash volumes are 150 μL and all shaking incubations are done on an Eppendorf Thermomixer set at 25° C., 800 rpm. Equilibration mixes are removed by pipetting, and plates are washed twice for 1 minute with buffer PB1 supplemented with 1 mM dextran sulfate and 500 μM biotin, then 4 times for 15 seconds with buffer PB1. A freshly made solution of 1 mM NHS-PEO4-biotin in buffer PB1 (150 µL/well) is added, and plates are incubated for 5 minutes with shaking. The NHS-biotin solution is removed, and plates washed 3 times with buffer PB1 supplemented with 20 mM glycine, and 3 times with buffer PB1. Eighty-five µL of buffer PB1 supplemented with 1 mM DxSO4 is then added to each well, and plates are irradiated under a BlackRay UV lamp (nominal wavelength 365 nm) at a distance of 5 cm for 20 minutes with shaking. Samples are transferred to a fresh, washed streptavidin-coated plate, or an unused well of the existing washed streptavidin plate, combining high and low sample dilution mixtures into a single well. Samples are incubated at room temperature with shaking for 10 minutes. Unadsorbed material is removed and the plates washed 8 times for 15 seconds each with buffer PB1 supplemented with 30% glycerol. Plates are then washed once with buffer PB1. Aptamers are eluted for 5 minutes at room temperature with 100 µL CAPSO elution buffer. 90 µL of the eluate is transferred to a 96-well HybAid plate and 10 µL neutralization buffer is added.

Semi-Automated Assay

Streptavidin plates bearing adsorbed equilibration mixes are placed on the deck of a BioTek EL406 plate washer, which is programmed to perform the following steps: unadsorbed material is removed by aspiration, and wells are washed 4 times with 300 µL of buffer PB1 supplemented with 1 mM dextran sulfate and 500 µM biotin. Wells are then washed 3 times with 300 µL buffer PB1. One hundred fifty µL of a freshly prepared (from a 100 mM stock in DMSO) solution of 1 mM NHS-PEO4-biotin in buffer PB1 is added. Plates are incubated for 5 minutes with shaking. Liquid is aspirated, and wells are washed 8 times with 300 µL buffer PB1 supplemented with 10 mM glycine. One hundred µL of buffer PB1 supplemented with 1 mM dextran sulfate are added. After these automated steps, plates are removed from the plate washer and placed on a thermoshaker mounted under a UV light source (BlackRay, nominal wavelength 365 nm) at a distance of 5 cm for 20 minutes. The thermoshaker is set at 800 rpm and 25° C. After 20 minutes irradiation, samples are manually transferred to a fresh, washed streptavidin plate (or to an unused well of the existing washed plate). High-abundance (3% serum+3% aptamer mix) and low-abundance reaction mixes (0.3% serum+0.3% aptamer mix) are combined into a single well at this point. This "Catch-2" plate is placed on the deck of BioTek EL406 plate washer, which is programmed to perform the following steps: the plate is incubated for 10 minutes with shaking. Liquid is aspirated, and wells are washed 21 times with 300 µL buffer PB1 supplemented with 30% glycerol. Wells are washed 5 times with 300 µL buffer PB1, and the final wash is aspirated. One hundred µL CAPSO elution buffer are added, and aptamers are eluted for 5 minutes with shaking. Following these automated steps, the plate is then removed from the deck of the plate washer, and 90 µL aliquots of the samples are transferred manually to the wells of a HybAid 96-well plate that contains 10 µL neutralization buffer.

Hybridization to Custom Agilent 8×15 k Microarrays

24 µL of the neutralized eluate is transferred to a new 96-well plate and 6 µL of 10× Agilent Block (Oligo aCGH/ChIP-on-chip Hybridization Kit, Large Volume, Agilent 5188-5380), containing a set of hybridization controls composed of 10 Cy3 aptamers is added to each well. Thirty µL 2× Agilent Hybridization buffer is added to each sample and mixed. Forty µL of the resulting hybridization solution is manually pipetted into each "well" of the hybridization gasket slide (Hybridization Gasket Slide, 8-microarray per slide format, Agilent). Custom Agilent microarray slides, bearing 10 probes per array complementary to 40 nucleotide random region of each aptamer with a 20× dT linker, are placed onto the gasket slides according to the manufacturers' protocol. The assembly (Hybridization Chamber Kit—SureHyb-enabled, Agilent) is clamped and incubated for 19 hours at 60° C. while rotating at 20 rpm.

Post Hybridization Washing

Approximately 400 mL Agilent Wash Buffer 1 is placed into each of two separate glass staining dishes. Slides (no more than two at a time) are disassembled and separated while submerged in Wash Buffer 1, then transferred to a slide rack in a second staining dish also containing Wash Buffer 1. Slides are incubated for an additional 5 minutes in Wash Buffer 1 with stirring. Slides are transferred to Wash Buffer 2 pre-equilibrated to 37° C. and incubated for 5 minutes with stirring. Slides are transferred to a fourth staining dish containing acetonitrile, and incubated for 5 minutes with stirring.

Microarray Imaging

Microarray slides are imaged with an Agilent G2565CA Microarray Scanner System, using the Cy3-channel at 5 µm resolution at 100% PMT setting, and the XRD option enabled at 0.05. The resulting TIFF images are processed using Agilent feature extraction software version 10.5.1.1 with the GE1_105_Dec08 protocol. Primary Agilent data is available as Supplementary Information (Figure S6).

Luminex Probe Design

Probes immobilized to beads have 40 deoxynucleotides complementary to the 3' end of the 40 nucleotide random region of the target aptamer. The aptamer complementary region is coupled to Luminex Microspheres through a hexaethyleneglycol (HEG) linker bearing a 5' amino terminus. Biotinylated detection deoxyoligonucleotides comprise 17-21 deoxynucleotides complementary to the 5' primer region of target aptamers. Biotin moieties are appended to the 3' ends of detection oligos.

Coupling of Probes to Luminex Microspheres

Probes are coupled to Luminex Microplex Microspheres essentially per the manufacturer's instructions, but with the following modifications: amino-terminal oligonucleotide amounts are 0.08 nMol per 2.5×106 microspheres, and the second EDC addition is 5 µL at 10 mg/mL. Coupling reactions are performed in an Eppendorf ThermoShaker set at 25° C. and 600 rpm.

Microsphere Hybridization

Microsphere stock solutions (about 40000 microspheres/4) are vortexed and sonicated in a Health Sonics ultrasonic cleaner (Model: T1.9C) for 60 seconds to suspend the microspheres. Suspended microspheres are diluted to 2000 microspheres per reaction in 1.5×TMAC hybridization solutions and mixed by vortexing and sonication. Thirty-three µL it per reaction of the bead mixture are transferred into a 96-well HybAid plate. Seven µL of 15 nM biotinylated detection oligonucleotide stock in 1×TE buffer are added to each reaction and mixed. Ten µL of neutralized assay sample are added and the plate is sealed with a silicon cap mat seal. The plate is first incubated at 96° C. for 5 minutes and incubated at 50° C. without agitation overnight in a conventional hybridization oven. A filter plate (Dura pore, Millipore part number MSBVN1250, 1.2 µm pore size) is prewetted with 75 µL 1×TMAC hybridization solution supplemented with 0.5% (w/v) BSA. The entire sample volume from the hybridization reaction is transferred to the filter plate. The hybridization plate is rinsed with 75 µL 1×TMAC hybridization solution containing 0.5% BSA and any remaining material is transferred to the filter plate. Samples are filtered under slow vacuum, with 1504 buffer evacuated over about 8 seconds. The filter plate is washed once with 75 µL it 1×TMAC hybridization solution containing 0.5% BSA and the microspheres in the filter plate are resuspended in 75 μL 1×TMAC hybridization solution containing 0.5% BSA. The filter plate is protected from light and incubated on an Eppendorf Thermalmixer R for 5 minutes at 1000 rpm. The filter plate is then washed once with 75 μL 1×TMAC hybridization solution containing 0.5% BSA. 75 μL of 10 μg/mL streptavidin phycoerythrin (SAPE-100, MOSS, Inc.) in 1×TMAC hybridization solution is added to each reaction and incubated on Eppendorf Thermalmixer R at 25° C. at 1000 rpm for 60 minutes. The filter plate is washed twice with 75μ 1×TMAC hybridization solution containing 0.5% BSA and the microspheres in the filter plate are resuspended in 75 μL 1×TMAC hybridization solution containing 0.5% BSA. The filter plate is then incubated protected from light on an Eppendorf Thermalmixer R for 5 minutes, 1000 rpm. The filter plate is then washed once with 75 μL 1×TMAC hybridization solution containing 0.5% BSA. Microspheres are resuspended in 75μ 1×TMAC hybridization solution supplemented with 0.5% BSA, and analyzed on a Luminex 100 instrument running XPonent 3.0 software. At least 100 microspheres are counted per bead type, under high PMT calibration and a doublet discriminator setting of 7500 to 18000.

QPCR Read-out

Standard curves for qPCR are prepared in water ranging from 108 to 102 copies with 10-fold dilutions and a no-template control. Neutralized assay samples are diluted 40-fold into diH2O. The qPCR master mix is prepared at 2× final concentration (2× KOD buffer, 400 μM dNTP mix, 400 nM forward and reverse primer mix, 2×SYBR Green I and 0.5 U KOD EX). Ten μL of 2× qPCR master mix is added to 10 μL of diluted assay sample. qPCR is run on a BioRad MyIQ iCycler with 2 minutes at 96° C. followed by 40 cycles of 96° C. for 5 seconds and 72° C. for 30 seconds.

The foregoing embodiments and examples are intended only as examples. No particular embodiment, example, or element of a particular embodiment or example is to be construed as a critical, required, or essential element or feature of any of the claims. Various alterations, modifications, substitutions, and other variations can be made to the disclosed embodiments without departing from the scope of the present application, which is defined by the appended claims. The specification, including the figures and examples, is to be regarded in an illustrative manner, rather than a restrictive one, and all such modifications and substitutions are intended to be included within the scope of the application. Steps recited in any of the method or process claims may be executed in any feasible order and are not limited to an order presented in any of the embodiments, the examples, or the claims. Further, in any of the aforementioned methods, one or more specifically listed biomarkers can be specifically excluded either as an individual biomarker or as a biomarker from any panel.

The invention claimed is:

1. A method of detecting protein levels of a set of biomarkers in a sample from a subject, comprising:
   (a) contacting a sample from a subject with a set of capture reagents, wherein the set of capture reagents comprises at least three capture reagents, wherein each capture reagent specifically binds to a different protein selected from: aminocylase-1(ACY1), sex hormone binding globulin (SHBG), capthepsin Z (CTSZ), c-met (MET), gelsolin (GSN), lower galectin-3 binding protein (LGALS3BP), tissue-type plasminogen activator (PLAT), neural cell adhesion molecule L-1 like protein (CHL1), antithrombin III (SERPINC1), sialic acid binding Ig like lectin 7(SIGLEC7), and sialic acid binding Ig like lectin 14 (SIGLEC14),
   (b) removing unbound capture reagents,
   (c) releasing bound capture reagents, and
   (d) detecting the amount of each released capture reagent, thereby detecting protein levels of a set of biomarkers in the sample from the subject.

2. The method of claim 1, wherein the method comprises detecting at least one, at least two, or three biomarkers selected from ACY1, SHBG, and SIGLEC 14.

3. The method of claim 1, wherein the method comprises detecting at least one, at least two, at least three, at least four, at least five, at least six, or seven biomarkers selected from ACY, SHBG, CTSZ, MET, GSN, LGALS3BP, and SIGLEC7.

4. The method of claim 1, wherein the method comprises detecting at least three proteins selected from ACY1, SHBG, CTSZ, MET, GSN, LGALS3BP, CHL1, and SERPINC1.

5. The method of claim 1, wherein the subject has been diagnosed with obesity, abdominal obesity, metabolic syndrome, cardiovascular disease, and/or diabetes.

6. The method of claim 1, wherein each capture reagent is an antibody or an aptamer.

7. The method of claim 6, wherein each capture reagent is an aptamer.

8. The method of claim 7, wherein at least one aptamer comprises at least one nucleotide with a modification.

9. The method of claim 8, wherein each aptamer binds to its target protein with an off rate ($t^{1/2}$) of ≥30 minutes.

10. The method of claim 1, wherein the sample is selected from a serum sample and a plasma sample.

11. The method of claim 1, further comprising administering to and/or prescribing to the subject at least one therapeutic agent selected from pioglitazone, vitamin E, and metformin.

12. The method of claim 1, wherein each capture reagent is an antibody.

13. The method of claim 1, wherein each capture reagent is detectably labeled.

14. The method of claim 1, wherein each capture reagent is detectably labeled with a fluorescent or chemiluminescent label.

15. The method of claim 1, wherein the set of capture reagents is immobilized on a solid support.

16. The method of claim 1, wherein the method comprises detecting ACY1, LGALS3BP, and SERPINC1.

* * * * *